(12) United States Patent
Fujinuma et al.

(10) Patent No.: US 11,193,212 B2
(45) Date of Patent: Dec. 7, 2021

(54) SYNTHETIC METHOD AND SYNTHETIC SYSTEM

(71) Applicant: SEKISUI CHEMICAL CO., LTD., Osaka (JP)

(72) Inventors: Naohiro Fujinuma, Glassboro, NJ (US); Kenichi Shinmei, Tsukuba (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 227 days.

(21) Appl. No.: 16/141,201

(22) Filed: Sep. 25, 2018

(65) Prior Publication Data

US 2020/0095692 A1 Mar. 26, 2020

(51) Int. Cl.
| | |
|---|---|
| C07C 68/00 | (2020.01) |
| C07C 68/06 | (2020.01) |
| C07C 68/08 | (2006.01) |
| C07C 271/00 | (2006.01) |
| C25B 3/23 | (2021.01) |
| C25B 3/26 | (2021.01) |
| C07C 69/96 | (2006.01) |
| C07C 271/10 | (2006.01) |
| C08G 64/02 | (2006.01) |
| C08G 71/00 | (2006.01) |
| C25B 15/08 | (2006.01) |
| C07C 269/04 | (2006.01) |

(52) U.S. Cl.
CPC ............... *C25B 3/23* (2021.01); *C07C 69/96* (2013.01); *C07C 271/10* (2013.01); *C08G 64/0208* (2013.01); *C08G 71/00* (2013.01); *C25B 15/08* (2013.01); *C07C 68/06* (2013.01); *C07C 269/04* (2013.01)

(58) Field of Classification Search
CPC ....... C07C 68/00; C07C 271/00; C07C 68/06; C07C 68/08; C25B 3/02; C25B 3/23; C25B 3/26
USPC .......................................... 568/300; 205/439
See application file for complete search history.

(56) References Cited

U.S. PATENT DOCUMENTS

| 6,262,226 B1 * | 7/2001 | Moore ................. B01J 19/1887 528/480 |
| 2013/0105330 A1 * | 5/2013 | Teamey .................. C07C 29/58 205/349 |

(Continued)

FOREIGN PATENT DOCUMENTS

WO 2014/046792 3/2014

OTHER PUBLICATIONS

Yu et al., "Electrosynthesis of Dimethyl Carbonate from Methanol and Carbon Monoxide under Mild Conditions," Industrial & Engineering Chemistry Research (May 29, 2013), vol. 52, No. 21, pp. 6901-6907. (Year: 2013).*

(Continued)

*Primary Examiner* — Edna Wong
(74) *Attorney, Agent, or Firm* — Wenderoth, Lind & Ponack, L.L.P.

(57) ABSTRACT

Provided is a synthesis method comprising a first step of producing a carbonate compound from carbon monoxide and an alcohol-based compound at an anode of a first electrochemical cell comprising a cathode and the anode, and a second step of synthesizing a first product by a dealcoholization reaction of the carbonate compound, wherein an alcohol-based compound eliminated in the second step is recycled in the first step.

13 Claims, 7 Drawing Sheets

(56) References Cited

U.S. PATENT DOCUMENTS

2018/0195184 A1* 7/2018 Fleischer .................. C25B 1/00
2019/0032228 A1* 1/2019 Krause ..................... C25B 9/08

OTHER PUBLICATIONS

Otsuka et al., "Electrolytic Carbonylation of Methanol Over the CuCl2 Anode in the Gas Phase," Journal of the Electrochemical Society (Jan. 1995), vol. 142, No. 1, pp. 130-135. (Year: 1995).*

Park et al., "Preparation of High-Molecular-Weight Aliphatic Polycarbonates by Condensation Polymerization of Diols and Dimethyl Carbonate," Macromolecules (May 14, 2013), vol. 46, No. 9, pp. 3301-3308. (Year: 2013).*

Li et al., "Electrolytic CO2 Reduction in Tandem with Oxidative Organic Chemistry," ACS Central Science (Jul. 26, 2017), vol. 3, No. 7, pp. 778-783. (Year: 2017).*

Duval et al., "Synthesis and Properties of Renewable Nonisocyanate Polyurethanes (NIPUs) from Dimethylcarbonate," Journal of Polymer Science Part A: Polymer Chemistry (Jun. 1, 2015), vol. 53, No. 11, pp. 1351-1359. (Year: 2015).*

Akiyasu Funakawa et al., "High Efficient Electrochemical Carbonylation of Methanol to Dimethyl Carbonate by $Br_2$/Br-Mediator System over Pd/C Anode", Journal of the Electrochemical Society, 153(4), D68-D73 (2006).

International Search Report and Written Opinion of the International Searching Authority dated Jan. 20, 2020, in International (PCT) Application No. PCT/JP2019/038829.

Cipris et al., "Anodic Synthesis of Organic Carbonates", J. Electrochem. Soc., vol. 125, No. 12, Dec. 1978, pp. 1954-1959.

Juliane Kupfernagel, "Discovering advantageous potential of Economy of Chain supply chains: A concept to extend Industrial Symbiosis", Master of Science, Mar. 5, 2015, pp. 82-95.

* cited by examiner

[Fig. 1]
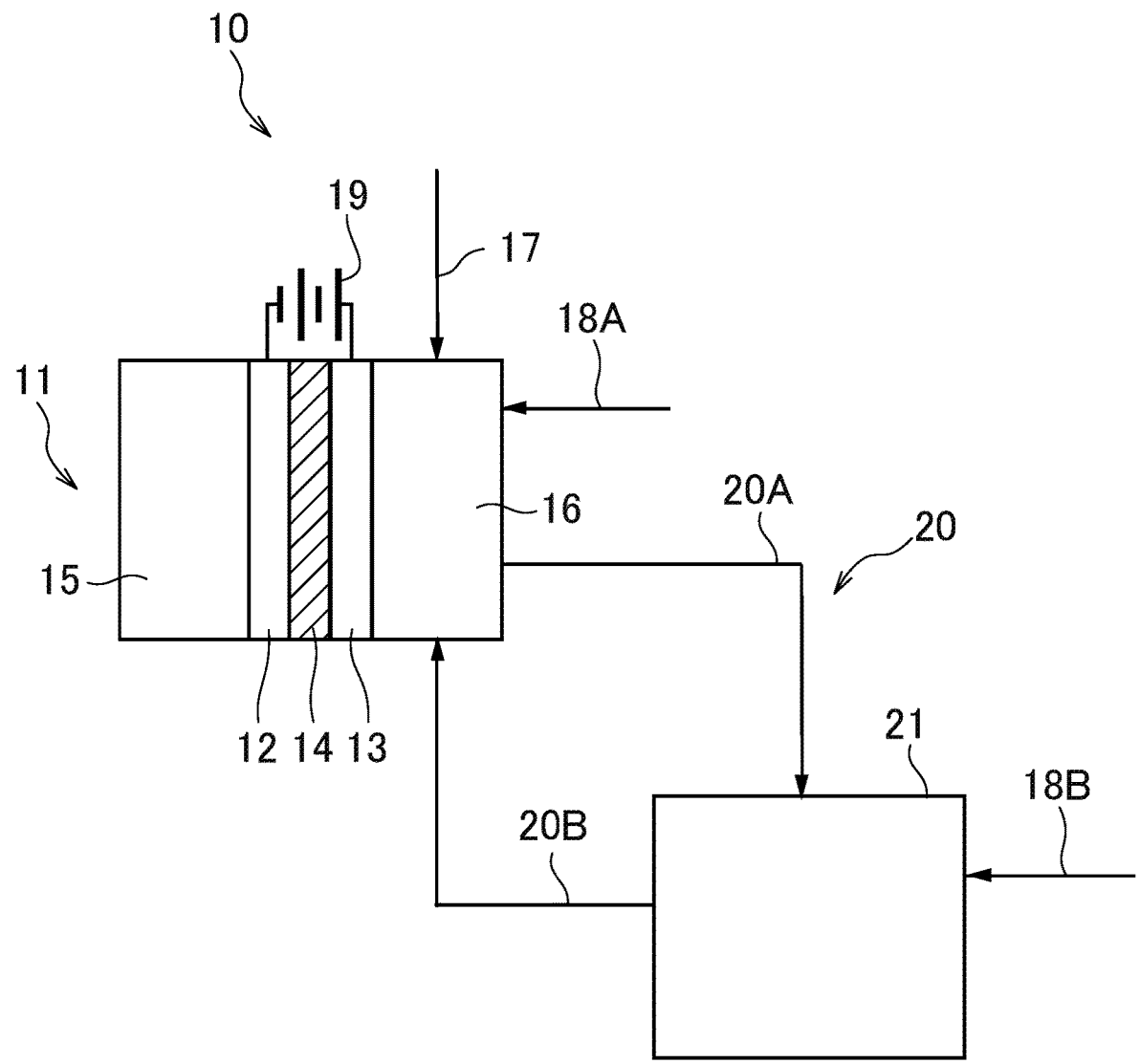

[Fig. 2]
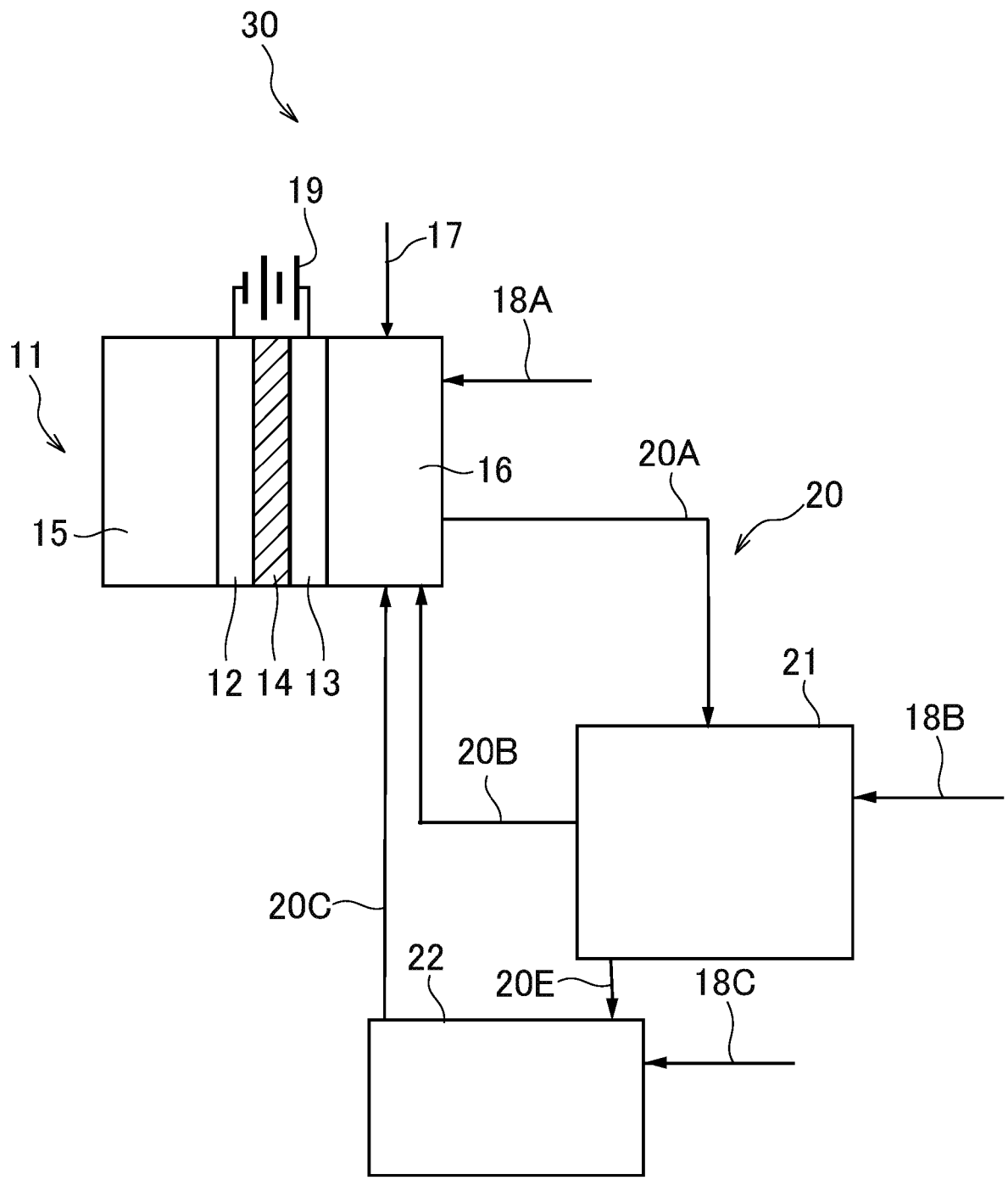

[Fig. 3]
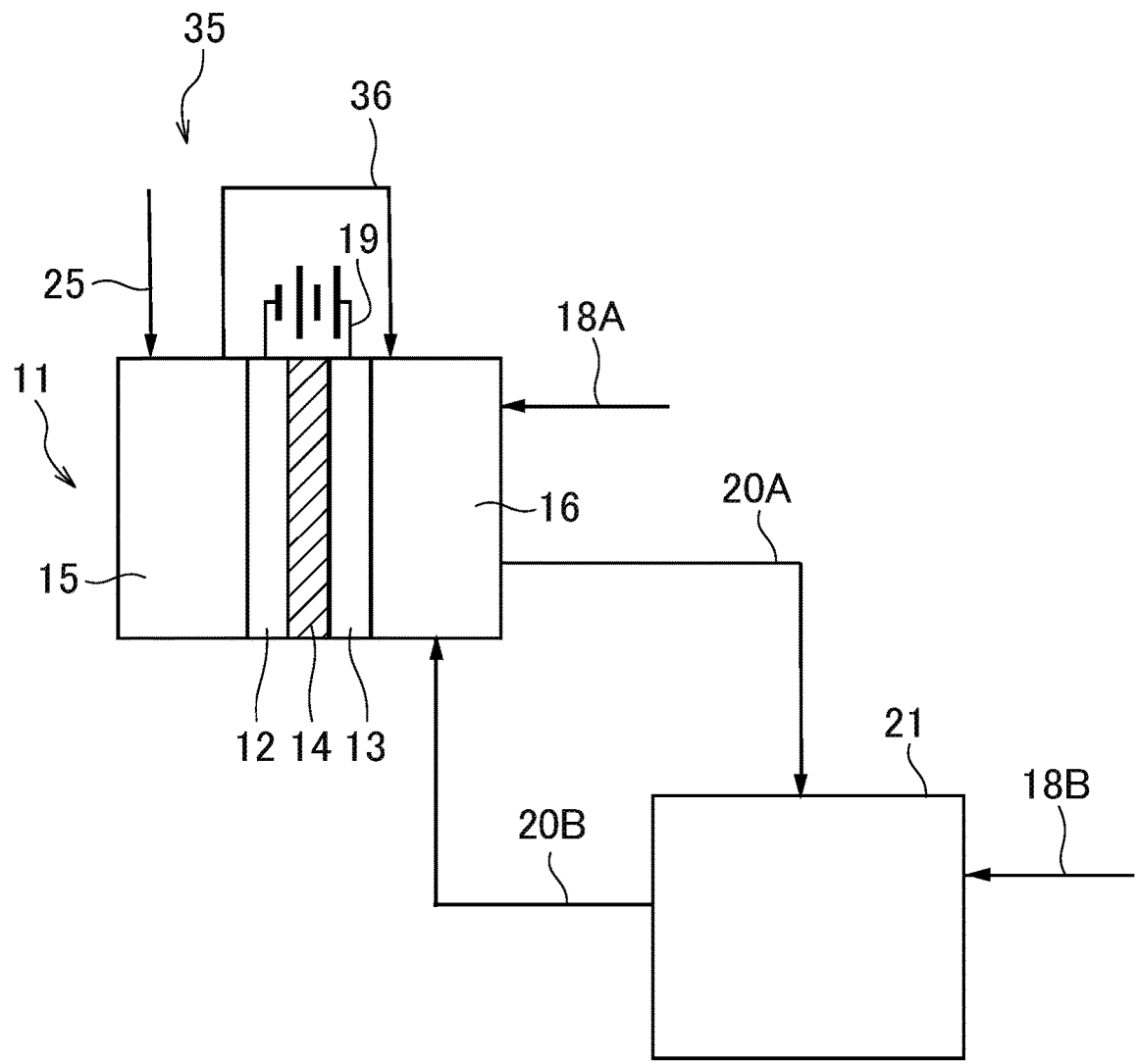

[Fig. 4]
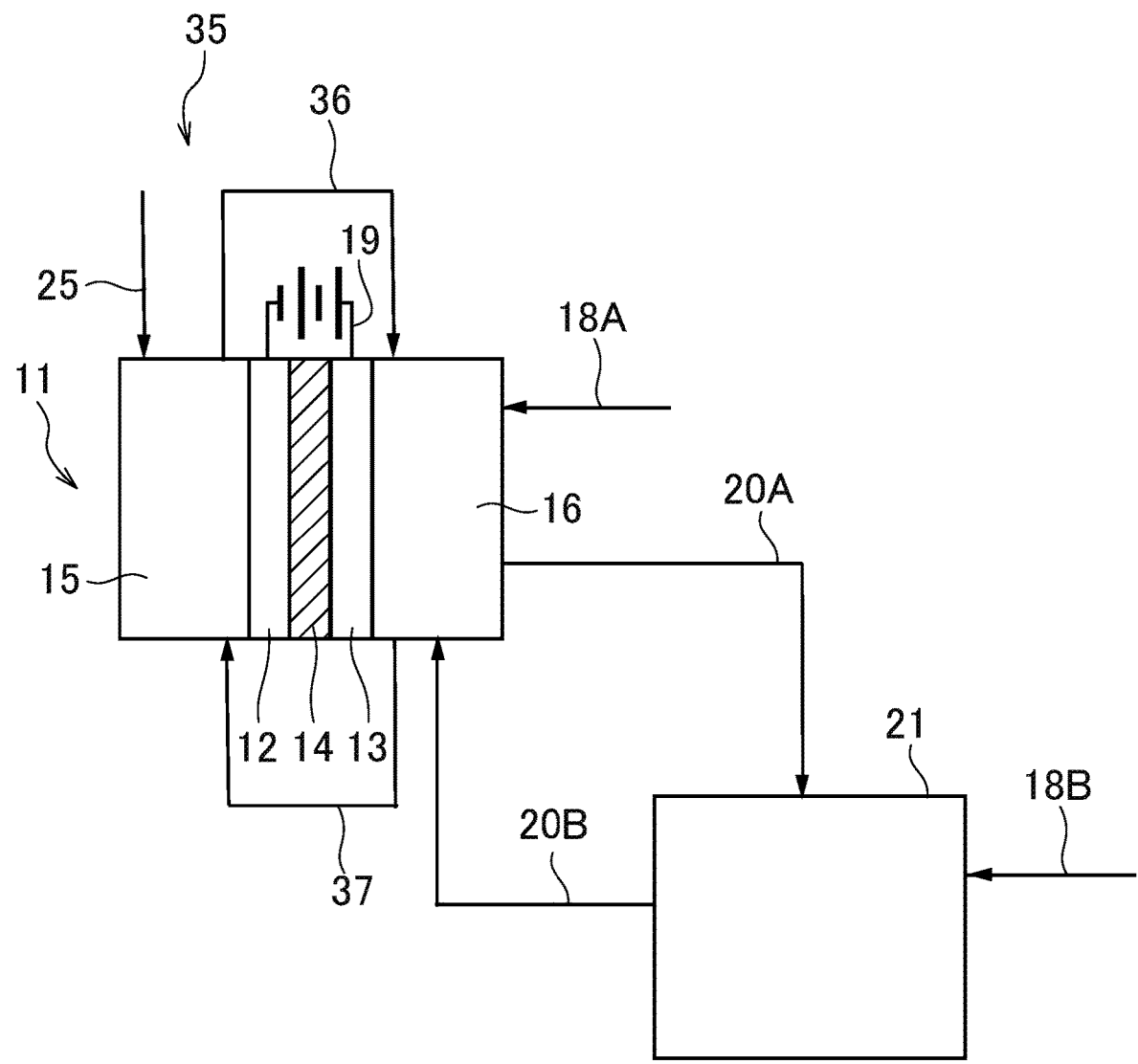

[Fig. 5]
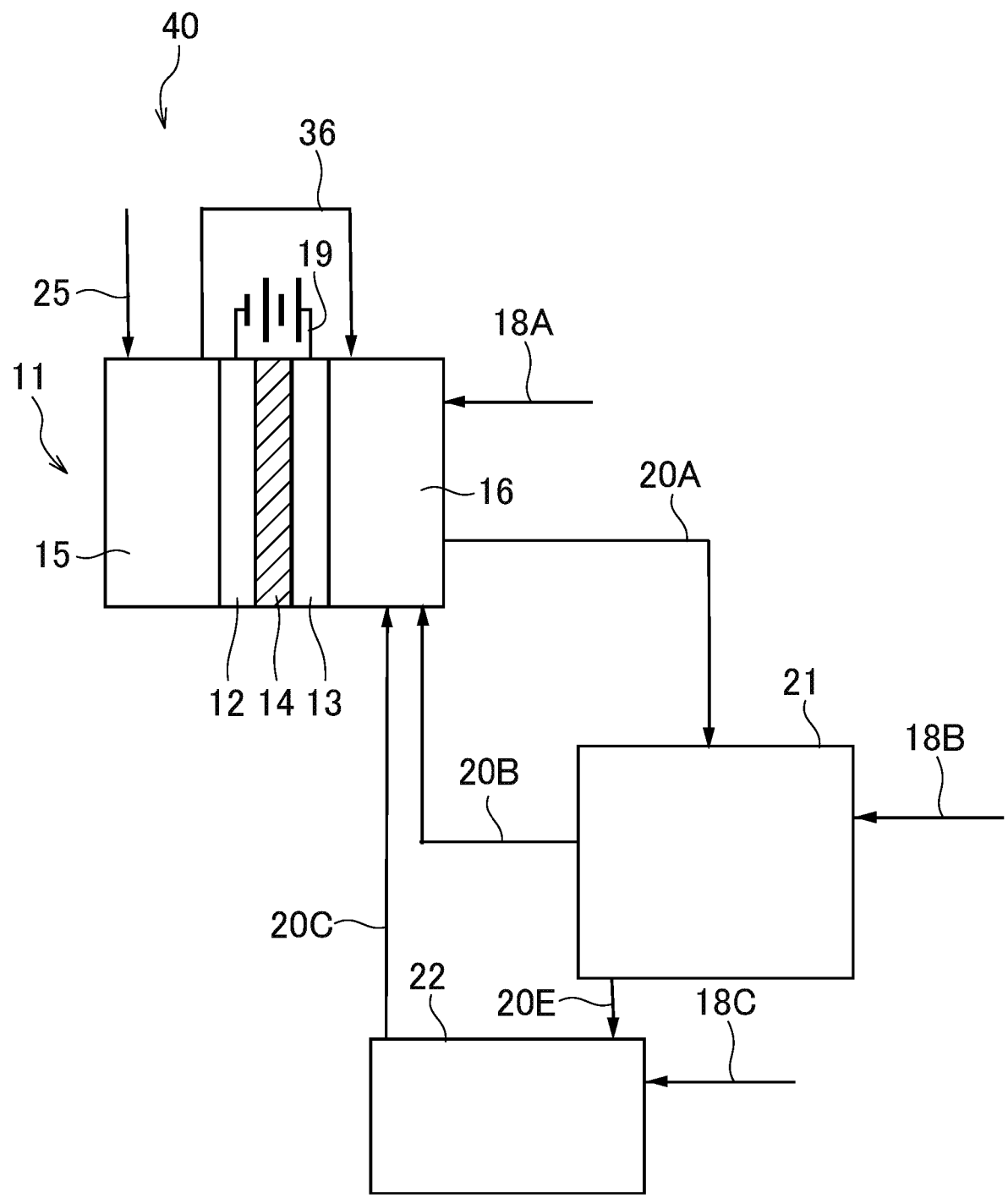

[Fig. 6]
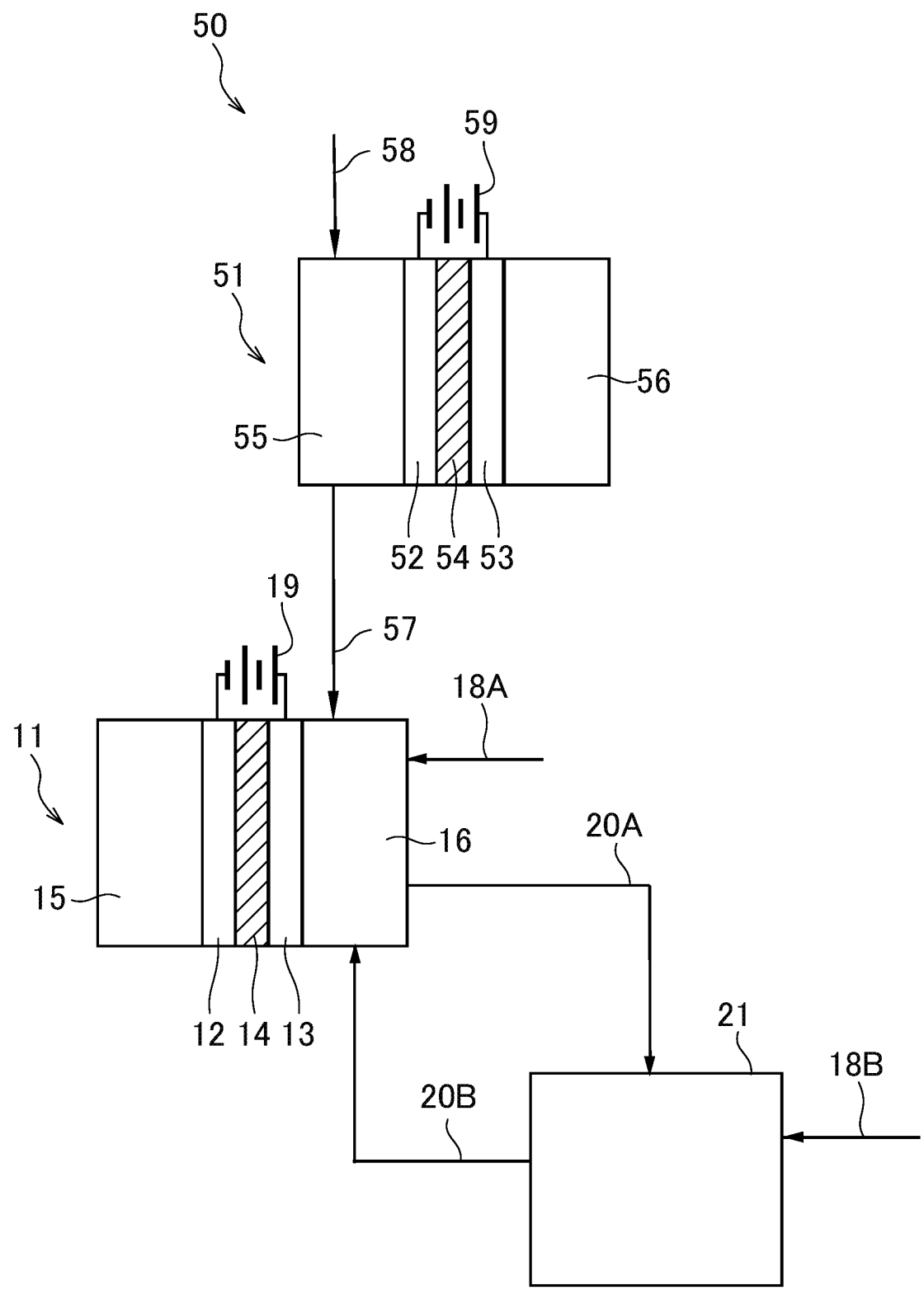

[Fig. 7]
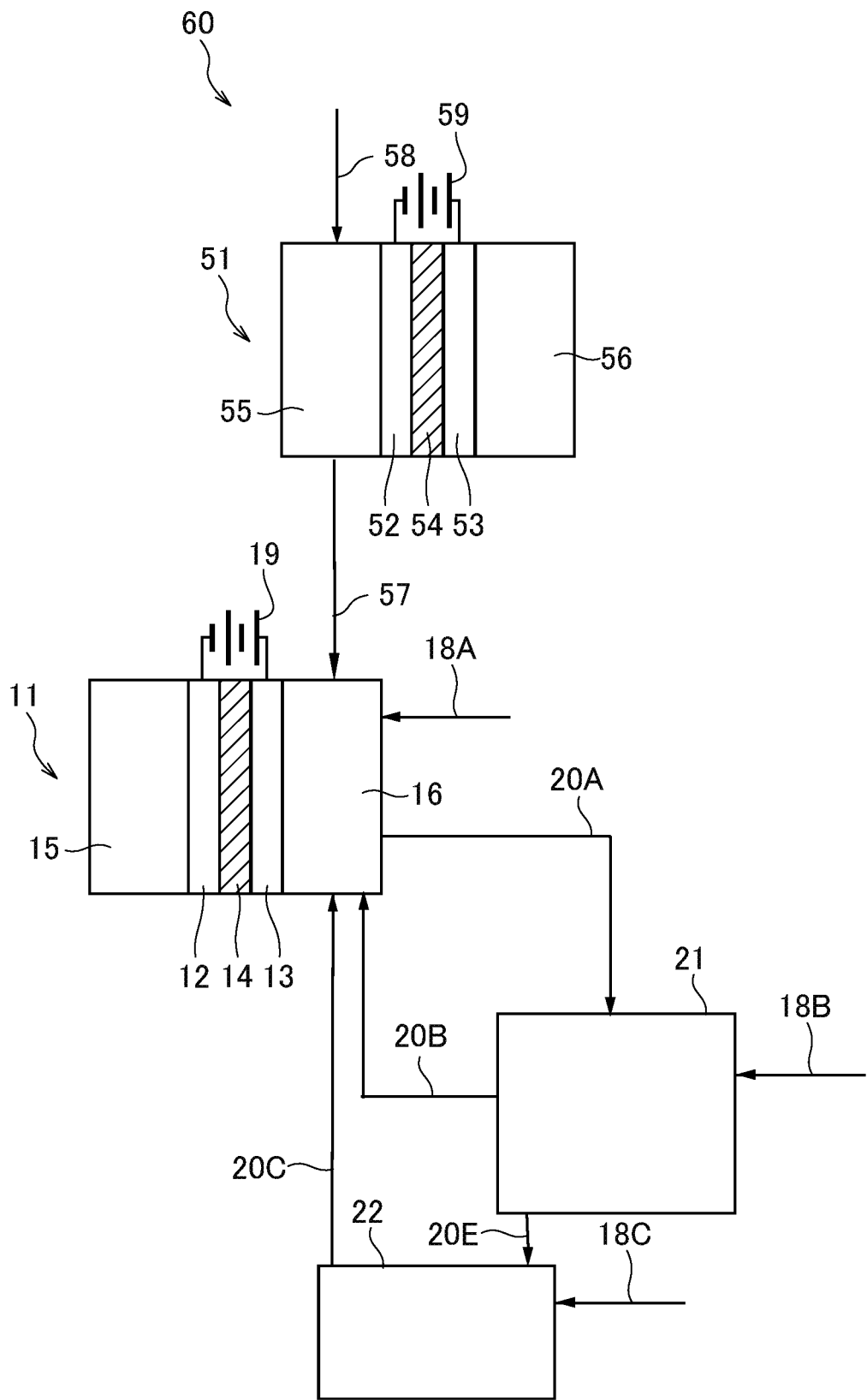

SYNTHETIC METHOD AND SYNTHETIC SYSTEM

TECHNICAL FIELD

The present invention relates to a synthesis method and a synthesis system in which an organic compound is synthesized with carbon monoxide as a raw material by an electrochemical reaction and a subsequent synthesis reaction.

BACKGROUND ART

In recent years, there has been studied production of valuable chemicals by electrical reduction of carbon dioxide for the purposes of suppression of global warming, replacing fossil fuels, and the like. There has also been attempted to synthesize organic compounds by use of carbon monoxide which is produced together with carbon dioxide in burning of fossil fuels, waste and the like, or which is obtained by reduction of carbon dioxide.

For example, NPL1 discloses synthesis of dimethyl carbonate from carbon monoxide and methanol at an anode by use of an electrochemical cell as an electrochemical reaction.

In addition, PTL1 discloses not only production of various valuable chemicals such as carbon monoxide by reduction of carbon dioxide at a side of a cathode, but also reduction of hydrogen halide to halogen at a side of an anode. In PTL1, halogen obtained by the reduction at a side of an anode reacts with an organic substance such as hydrocarbon at a reactor provided separately from an electrochemical cell, and thus is converted into a halogenated organic compound. While the halogenated organic compound is converted into valuable chemicals such as alcohol due to elimination of halogen, eliminated halogen is again fed as hydrogen halide to the side of the anode and recycled.

CITATION LIST

Patent Literature

PTL1: WO2014/046792

Non Patent Literature

NPL1: Journal of the Electrochemical Society, 153 (4), D68 (2006)

SUMMARY OF INVENTION

Various compounds obtained by an electrochemical reaction are generally converted into highly useful organic compounds subsequently through multiple reaction steps. Accordingly, not only an electrochemical reaction, but also subsequent reactions are needed to be efficiently performed, in order to provide highly useful organic compounds from carbon dioxide, carbon monoxide, and the like as raw materials. NPL1, however, discloses neither any reaction to be conducted after production of a carbonate compound, nor any method which can practically produce a valuable organic compound by means of an electrochemical reaction.

Moreover, a by-product of an organic compound is generally produced in the course of providing an objective compound in an organic synthesis reaction, and use of the by-product is important for the attainment of efficient production. PTL1 discloses both an electrochemical reaction in an electrochemical cell and a subsequent reaction step, but does not disclose any configuration where a by-product of an organic compound is recycled in the electrochemical reaction, and thus cannot be said to indicate a sufficiently efficient reaction scheme.

An object of the present invention is to provide a method which can efficiently and practically synthesize an organic compound by recycle of a by-product of an organic compound produced in a subsequent reaction, for an electrochemical reaction, where carbon monoxide is adopted as a starting material.

The gist of the present invention is as follows.

[1] A synthesis method comprising:
a first step of producing a carbonate compound from carbon monoxide and an alcohol-based compound at a side of an anode of a first electrochemical cell comprising a cathode and the anode; and
a second step of synthesizing a first product by a dealcoholization reaction of the carbonate compound,
wherein an alcohol-based compound eliminated in the second step is recycled in the first step.

[2] The synthesis method according to [1], wherein the carbonate compound is at least one selected from the group consisting of dimethyl carbonate, diethyl carbonate, ethylene carbonate, dipropyl carbonate, propylene carbonate, ethyl methyl carbonate, methyl propyl carbonate, ethyl propyl carbonate and diphenyl carbonate.

[3] The synthesis method according to [1] or [2], wherein the first product is synthesized by a dealcoholization condensation reaction of the carbonate compound with at least one selected from the group consisting of a diol-based compound and a diamine-based compound, in the second step.

[4] The synthesis method according to [3], wherein the first product is at least one selected from the group consisting of compounds represented by the following formulae (4-1) and (5-1):

(4-1)

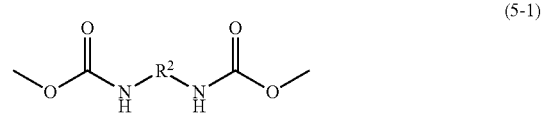

(5-1)

wherein $R^1$ and $R^2$ each independently represent an organic group having 1 to 30 carbon atoms.

[5] The synthesis method according to [3], wherein the first product is a polymer having at least any of repeating units represented by the following formulae (4-2) and (5-2):

(4-2)

(5-2)

wherein $R^1$ and $R^2$ each independently represent an organic group having 1 to 30 carbon atoms.

[6] The synthesis method according to any of [1] to [5], wherein
the second step is performed in a first reactor,
the method further comprises a third step of synthesizing a second product by a further dealcoholization reaction of the first product in a second reactor that is a separate reactor from the first reactor, and
an alcohol-based compound eliminated in the third step is recycled in the first step.

[7] The synthesis method according to [6], wherein the second product is a polymer having at least any of repeating units represented by the following formulae (4-2) and (5-2):

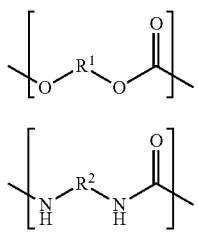

wherein $R^1$ and $R^2$ each independently represent an organic group having 1 to 30 carbon atoms.

[8] The synthesis method according to any of [1] to [7], wherein at least a part of the carbon monoxide is produced by reduction of carbon dioxide at the side of the cathode of the first electrochemical cell.

[9] The synthesis method according to any of [1] to [8], wherein at least a part of the carbon monoxide is produced at a side of a cathode of a second electrochemical cell that is a separate electrochemical cell from the first electrochemical cell.

[10] A synthesis system comprising:
a first electrochemical cell comprising a cathode and an anode, wherein the anode comprises a catalyst that catalyzes a reaction for production of a carbonate compound from carbon monoxide and an alcohol-based compound;
a first gas feed line that feeds carbon monoxide to the side of the anode of the first electrochemical cell;
a first reactor that produces a first product by a dealcoholization reaction of the carbonate compound; and
a circulation line configured so as to enable the carbonate compound produced at the side of the anode of the first electrochemical compartment to be fed to the first reactor and enable an alcohol-based compound eliminated in the first reactor to be fed to the side of the anode of the first electrochemical cell.

[11] The synthesis system according to [10], comprising:
a second reactor that produces a second product by a dealcoholization reaction of the first product produced in the first reactor; and
a feed pathway that feeds an alcohol-based compound eliminated in the second reactor, to the side of the anode of the first electrochemical cell.

[12] The synthesis system according to [10] or [11], comprising a second gas feed line that feeds carbon dioxide to the side of the cathode of the first electrochemical cell, wherein
the cathode of the first electrochemical cell comprises a catalyst that reduces carbon dioxide to carbon monoxide; and
the first gas feed line is a connecting path that connects the side of the cathode of the first electrochemical cell to the side of the anode thereof.

[13] The synthesis system according to any of [10] to [12], comprising:
a second electrochemical cell comprising a cathode and an anode, wherein the cathode comprises a catalyst that reduces carbon dioxide to carbon monoxide; and
a third gas feed line that feeds carbon dioxide to the side of the cathode of the second electrochemical cell,
wherein the first gas feed line is a connecting path that connects the side of the cathode of the second electrochemical cell and the side of the anode of the first electrochemical cell.

BRIEF DESCRIPTION OF DRAWINGS

FIG. 1 is a schematic view of a synthesis system according to a first embodiment.
FIG. 2 is a schematic view of a synthesis system according to a second embodiment.
FIG. 3 is a schematic view of a synthesis system according to a third embodiment.
FIG. 4 is a schematic view of a synthesis system according to a variant of the third embodiment.
FIG. 5 is a schematic view of a synthesis system according to a fourth embodiment.
FIG. 6 is a schematic view of a synthesis system according to a fifth embodiment.
FIG. 7 is a schematic view of a synthesis system according to a sixth embodiment.

DESCRIPTION OF EMBODIMENTS

Hereinafter, the synthesis method and the synthesis system of the present invention will be described with reference to embodiments.

First Embodiment

A synthesis system 10 according to a first embodiment of the present invention comprises a first electrochemical cell 11 comprising a cathode 12 and an anode 13, and a first reactor 21.

In the first electrochemical cell 11, a step of producing a carbonate compound from carbon monoxide and an alcohol-based compound at the side of the anode (first step) is performed. In the first reactor 21, a step of synthesizing a first product by a dealcoholization reaction of the carbonate compound obtained in the first electrochemical cell 11 (second step) is performed, and an alcohol-based compound eliminated in the second step is recycled in the first step.

In the present embodiment, an alcohol-based compound produced as a by-product in synthesis of the first product can be recycled in an electrochemical reaction performed in the first electrochemical cell 11, and therefore the first product can be efficiently and practically synthesized.

In the following description, an alcohol-based compound used as a raw material in the first step and eliminated in the second step may be referred to as an "alcohol-based compound (1)".

Hereinafter, the present embodiment will be described in more detail.

[First Electrochemical Cell]

The first electrochemical cell 11 in the present embodiment comprises not only the cathode 12 and the anode 13, but also an ion conducting membrane 14, therein. The first electrochemical cell 11 has a two-chamber membrane-type cell-structure in which the cell is partitioned by the ion conducting membrane 14 and separated to two chambers, to allow a first electrochemical compartment 15 and a second electrochemical compartment 16 to be formed. The first electrochemical compartment 15 and the second electrochemical compartment 16 are provided with the cathode 12 and the anode 13 disposed therein, respectively, and form a region at the side of the cathode 12 (cathode region) and a region at the side of the anode 13 (anode region), respectively.

The cathode 12 and the anode 13 are, for example, disposed on and jointed to each surface of the ion conducting membrane 13, respectively, and are taken together with the ion conducting membrane 14 to form a membrane-electrode assembly, as illustrated in FIG. 1. A power source 19 is connected to the cathode 12 and the anode 13, and a voltage is applied between the cathode 12 and the anode 13 with the power source 19.

<First Electrochemical Compartment>

The cathode 12 disposed in the first electrochemical compartment 15 comprises a catalyst for reduction (first catalyst). The catalyst for reduction is not particularly limited, and various metals or metal compounds, or a carbon compound containing at least any of heteroelements or metals can be used.

A compound that can be reduced by a catalyst for reduction (hereinafter, such a compound being also referred to as a "reducible compound") may be disposed in the first electrochemical compartment 15. The reducible compound is not particularly limited, and examples thereof include water, carbon dioxide, carbon monoxide and acrylonitrile.

The reducible compound is not particularly limited as long as the compound is disposed in the first electrochemical compartment 15, and, when a gas such as carbon dioxide is adopted as the reducible compound, the reducible compound may be flown into the first electrochemical compartment 15. When water is adopted as the reducible compound, the first electrochemical compartment 15 may be filled with water.

Furthermore, the first electrochemical compartment 15 may be filled with a filling liquid such as water or an electrolyte solution to allow the reducible compound to be dissolved in the water or electrolyte solution, or the reducible compound in the form of gas may be flown into water or an electrolyte solution. Alternatively, the first electrochemical compartment 15 may not be filled with any filling liquid such as water or an electrolyte solution and the reducible compound in the form of gas may be fed into the first electrochemical compartment 15 filled with no filling liquid.

(Catalyst for Reduction)

The catalyst for reduction (first catalyst) contained in the cathode 12 is not particularly limited as long as it catalyzes reduction of the reducible compound. For example, various metals, metal compounds, or a carbon compound containing at least any of heteroelements or metals can be used as the catalyst for reduction.

Examples of such metals include V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce and Nd.

Metal-inorganic compounds and metal-organic compounds of these metals can be each used as such a metal compound, and specific examples include metal halides, metal oxides, metal hydroxides, metal nitrates, metal sulfates, metal acetates, metal phosphates, metal carbonyls and metal acetylacetonates.

When the reducible compound is carbon dioxide, preferable specific examples of the metal element include Sb, Bi, Sn, Pb, Ni, Ru, Co, Rh, Cu, Ag, Mn, Fe and Zn, and among them, Bi, Sb, Ni, Co, Ru and Ag are more preferable.

Examples of the carbon compound containing at least any of the heteroelements or metals include nitrogen-containing graphite, nitrogen-containing carbon nanotube, nitrogen-containing graphene, Ni- and nitrogen-containing graphite, Ni- and nitrogen-containing carbon nanotube, Ni- and nitrogen-containing graphene, Cu- and nitrogen-containing graphite, Cu- and nitrogen-containing carbon nanotube, Cu- and nitrogen-containing graphene, Co- and nitrogen-containing graphite, Co- and nitrogen-containing carbon nanotube, and Co- and nitrogen-containing graphene.

The cathode 12 may contain, in addition to the catalyst for reduction, a conductive carbon material for imparting electrical conductivity, provided that, when the carbon compound is used as the catalyst for reduction, the carbon compound also serves as the conductive carbon material. Various carbon materials having electrical conductivity can be each used as the conductive carbon material, and examples include carbon blacks such as activated carbon, Ketjen black, acetylene black and mesoporous carbon, graphite, carbon fibers, carbon paper, and carbon whiskers. Such a carbon compound may be mixed with a complex containing any of the metals, and calcinated and formed into a catalyst powder or the like.

The cathode 12 is preferably a conductive carbon material such as carbon paper, which is provided with at least any of the metals and metal compounds supported thereon, or at least any of the metals and metal compounds, and a conductive carbon material, supported thereon. The supporting method is not limited, and, for example, may include dispersing such metal or metal compound, the catalyst powder, or the like in a solvent, coating a conductive carbon material such as carbon paper with the resulting dispersion, and heating the resultant.

A fluorine-containing compound such as polytetrafluoroethylene (PTFE), tetrafluoroethylene oligomer (TFEO), graphite fluoride ((CF)n), and pitch fluoride (FP) may be mixed in the cathode 12. Such a compound is used as a water repellent agent, and enhances the electrochemical reaction efficiency. The fluorine-containing compound can also be used as a binder in formation of the cathode 12. In this case, for example, the cathode may be produced by dispersing the catalyst for reduction and the fluorine-containing compound in a solvent, coating a conductive carbon material such as carbon paper with the resulting dispersion, and heating the resultant.

<Second Electrochemical Compartment>

A gas feed line 17 is connected to the second electrochemical compartment 16, and carbon monoxide is fed thereto through the gas feed line 17. Herein, a gas feed line that feeds carbon monoxide to the second electrochemical compartment 16 (namely, the side of the anode of the first electrochemical cell 11) may be referred to as a first gas feed line. Carbon monoxide is fed in the form of gas. The gas feed line 17 is configured from piping and the like and is connected to a carbon monoxide source not illustrated, or the like, and carbon monoxide is fed from the carbon monoxide source or the like.

A flow rate adjusting mechanism or the like may be provided on the gas feed line 17, and may adjust the flow rate of carbon monoxide to be fed. Carbon monoxide may be continuously or intermittently fed to the second electrochemical compartment 16. Carbon monoxide may be fed, as carbon monoxide itself, to the second electrochemical compartment 16, or may be fed, together with an inert gas such as helium as a carrier gas, to the second electrochemical compartment 16. Furthermore, carbon monoxide may be fed together with a carbon dioxide gas or the like.

Carbon monoxide may be fed, with bubbling or the like, to a filling liquid (alcohol-based compound (1), mixed liquid, or the like) mentioned below with which the second electrochemical compartment 16 is filled. Alternatively, carbon monoxide may be at least partially dissolved in a filling liquid with which the second electrochemical compartment 16 is filled, and then reacted with the alcohol-based compound (1) in the second electrochemical compartment 16.

The second electrochemical compartment 16 is filled with the alcohol-based compound (1). The alcohol-based compound (1) may be, for example, fed from the first reactor 21 or fed through a raw material feed port 18A provided on the second electrochemical compartment 16, as described below. Herein, the raw material feed port 18A is a feed port configured from piping or the like, through which a raw material is fed from any other than the first reactor 21. The alcohol-based compound (1) may be in any form of a solid, a liquid or gas under the environment where an electrochemical reaction is performed in the second electrochemical compartment 16, and is preferably in the form of a liquid. When the alcohol-based compound (1) is in the form of a solid or gas, or the solubility of a third catalyst or the like described below is needed to be enhanced, the second electrochemical compartment 16 may be filled with the alcohol-based compound (1) in the form of a mixed liquid with a solvent (hereinafter, also simply referred to as a "mixed liquid"). Herein, the second electrochemical compartment 16 may be fully filled with the alcohol-based compound (1) or the mixed liquid, or may partially have a space.

(Alcohol-Based Compound (1))

The alcohol-based compound (1) in the present invention can be reacted with carbon monoxide to produce a carbonate compound in the second electrochemical compartment 16. The alcohol-based compound (1) is a compound having at least one hydroxyl group, more specifically, a compound represented by the following general formula (1).

In the present specification, the "alcohol-based compound" also encompasses an aromatic hydroxy compound in which a hydroxyl group is directly bound to an aromatic ring such as a benzene ring, representative examples thereof including phenol, as described below.

ROH (1)

R represents an organic group having 1 to 15 carbon atoms.

Examples of the organic group having 1 to 15 carbon atoms, represented by R in the general formula (1), include a hydrocarbon group having 1 to 15 carbon atoms. Examples of the hydrocarbon group include an alkyl group having 1 to 15 carbon atoms or an alkenyl group having 2 to 15 carbon atoms, and an aryl group having 6 to 15 carbon atoms.

Examples of the alkyl group having 1 to 15 carbon atoms include a methyl group, an ethyl group, various propyl groups, various butyl groups, various pentyl groups, various hexyl groups, various heptyl groups, various octyl groups, various nonyl groups, various decyl groups, various dodecyl groups, and various pentadecyl groups.

Examples of the alkenyl group having 2 to 15 carbon atoms include a vinyl group, various propynyl groups, various butynyl groups, various pentynyl groups, various hexenyl groups, various heptenyl groups, various octenyl groups, various nonenyl groups, various decenyl groups, various dodecenyl groups, and various pentadecenyl groups.

Herein, the term "various" means various isomers including n-, sec-, tert-, and iso-groups. The alkyl group or the alkenyl group may be any of linear, branched or cyclic.

Examples of the aryl group having 6 to 15 carbon atoms include a phenyl group and a naphthyl group. The above hydrocarbon group may have a substituent, and in this case, the number of carbon atom(s) of such a hydrocarbon group also including the substituent is 1 to 15.

The organic group having 1 to 15 carbon atoms in the general formula (1) may contain a hetero atom such as a nitrogen atom, an oxygen atom, a sulfur atom, a phosphorus atom, and/or a halogen atom.

Among them, an oxygen atom is preferable. When the organic group has an oxygen atom, the oxygen atom is preferably an oxygen atom derived from any of an alcohol group and an ether bond. Accordingly, R preferably represents a hydrocarbon group having at least any of a hydroxyl group and an ether bond. In addition, the number of hydroxyl groups in R is preferably one. That is, the alcohol-based compound (1) may have two hydroxyl groups.

The alcohol-based compound (1) having two hydroxyl groups is, more specifically, preferably a group represented by the following formula (1-1).

HO—$R^{11}$—OH (1-1)

In the formula (1-1), $R^{11}$ represents a divalent saturated hydrocarbon group having 2 to 15 carbon atoms, and the number of carbon atoms in $R^{11}$ is preferably 2 to 4, more preferably 2 to 3.

The compound represented by the general formula (1) is, among the above, preferably a compound where R represents an alkyl group having 1 to 8 carbon atoms, an alkenyl group having 2 to 8 carbon atoms, or an aryl group having 6 to 8 carbon atoms, and is also preferably one represented by the general formula (1-1), where the number of carbon atoms in $R^{11}$ is 2 to 4.

Among them, a compound where R represents an alkyl group or an aryl group is more preferable, and, in particular, a compound where R represents an alkyl group is further preferable. The number of carbon atom(s) in the alkyl group is more preferably 1 to 3, further preferably 1 or 2.

Specifically, methanol, ethanol, phenol, 1-propanol, ethylene glycol, propylene glycol, and the like are preferable, and among them, methanol is more preferable, from the viewpoint of reactivity and production efficiency.

The alcohol-based compound (1) may be used singly or in combinations of two or more kinds thereof.

The reaction performed in the second electrochemical compartment 16 is a carbonylation reaction where a carbonate compound is produced from carbon monoxide and the alcohol-based compound (1), and specifically, a carbonate compound $((RO)_2CO)$ is produced by a reaction represented by the following formula (i).

$$CO+2ROH \rightarrow (RO)_2CO+2H^{+}+2e^{-}$$ (i)

In (i), R has the same meaning as above, and R preferably represents an alkyl group having 1 to 8 carbon atoms, an alkenyl group having 2 to 8 carbon atoms, or an aryl group having 6 to 8 carbon atoms, more preferably an alkyl group or an aryl group, further preferably an alkyl group. The number of carbon atom(s) in the alkyl group is more preferably 1 to 3, further preferably 1 or 2.

When ROH is represented by the general formula (1-1), a carbonate compound is produced by a reaction represented by the following (ii).

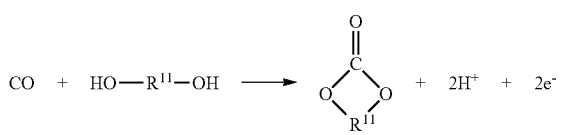

(ii)

In (ii), $R^{11}$ has the same meaning as above, and the number of carbon atoms in $R^{11}$ is preferably 2 to 4, more preferably 2 to 3.

Specific preferable examples of the carbonate compound include one or more selected from the group consisting of dimethyl carbonate, diethyl carbonate, ethylene carbonate, dipropyl carbonate, propylene carbonate, diphenyl carbonate, ethyl methyl carbonate, methyl propyl carbonate and ethyl propyl carbonate, and among them, dimethyl carbonate is more preferable.

A solvent usually used in an electrochemical reaction can be selected as the solvent that may be used together with the alcohol-based compound (1) in the second electrochemical compartment 16, and examples include nitrile-based solvents such as acetonitrile, carbonate-based solvents such as ethylene carbonate, propylene carbonate, butylene carbonate, vinylene carbonate, dimethyl carbonate, ethyl methyl carbonate and diethyl carbonate, lactone-based solvents such as γ-butyrolactone, ether-based solvents such as 1,2-dimethoxyethane, 1-ethoxy-2-methoxyethane, 1,2-diethoxyethane, tetrahydrofuran and 2-methyltetrahydrofuran, phosphate solvents, phosphoric acids, sulfolane-based solvents, and pyrrolidones. Such solvents may be used singly or in combinations of two or more kinds thereof.

Herein, an electrolyte salt is preferably added to the alcohol-based compound (1) or the mixed liquid as the filling liquid in the second electrochemical compartment from the viewpoint of an enhancement in electrochemical reaction efficiency. In such a case, the alcohol-based compound (1) or the mixed liquid itself serves as an electrolyte solution.

Examples of the electrolyte salt include an alkali metal salt, an alkali metal peroxide and an ammonium salt.

Specific examples of the alkali metal salt include lithium salts such as lithium hydroxide, lithium chloride, lithium bromide, lithium iodide, lithium hydrogen carbonate, lithium sulfate, lithium hydrogen sulfate, lithium phosphate and lithium hydrogen phosphate; sodium salts such as sodium hydroxide, sodium chloride, sodium bromide, sodium iodide, sodium hydrogen carbonate, sodium sulfate, sodium hydrogen sulfate, sodium phosphate and sodium hydrogen phosphate; and potassium salts such as potassium hydroxide, potassium chloride, potassium bromide, potassium iodide, potassium hydrogen carbonate, potassium sulfate, potassium hydrogen sulfate, potassium phosphate and potassium hydrogen phosphate.

Examples of the alkali metal peroxide include lithium peroxide and sodium peroxide.

Examples of the ammonium salt include ammonium chloride, ammonium bromide, ammonium iodide, ammonium perchlorate and tetrabutylammonium tetrafluoroborate.

Among the above, a lithium salt such as lithium bromide is preferable.

Such electrolyte salts may be used singly or in combinations of two or more kinds thereof.

The concentration of the electrolyte salt in the solution is, for example, in the range from 0.001 to 2 mol/L, preferably in the range from 0.01 to 1 mol/L.

(Anode)

The anode comprises a second catalyst that catalyzes a reaction for production of a carbonate compound from carbon monoxide and the alcohol-based compound (1). As the second catalyst, for example, a material comprising one or more selected from the group consisting of various metals, metal compounds and conductive carbon materials can be used.

The second catalyst preferably comprises at least one element of Group 8 to Group 12 as a metal, and examples of such a metal include iron, gold, copper, nickel, platinum, palladium, ruthenium, osmium, cobalt, rhodium and iridium. Metal-inorganic compounds and metal-organic compounds of these metals can be each used as such a metal compound, specific examples include metal halides, metal oxides, metal hydroxides, metal nitrates, metal sulfates, metal acetates, metal phosphates, metal carbonyls and metal acetylacetonates, and metal halides are preferable. Suitable specific examples of the metal halides include $PdCl_2$ (palladium chloride), $RuCl_3$, $RhCl_3$, $H_2PtCl_6$, $HAuCl_4$, $CuCl_3$, $CoCl_2$ and $NiCl_2$.

Various carbon materials having electrical conductivity can be each used as the conductive carbon material, and examples include carbon blacks such as mesoporous carbon, activated carbon, Ketjen black and acetylene black, graphite, carbon fibers, carbon paper, and carbon whiskers.

The anode 13 is, for example, a composite formed by mixing at least any of a metal and a metal compound with a conductive carbon material. The composite may be in the form of a composite film or a powder, for example. The composite can be formed by, for example, dispersing a mixture of at least any of a metal and a metal compound with a conductive carbon material in a solvent, and subjecting the resultant to calcinating.

The anode 13 is preferably a conductive carbon material such as carbon paper, which is provided with at least any of the metals and metal compounds supported thereon, or at least any of the metals and metal compounds, and a conductive carbon material, supported thereon. The supporting method is not limited, and, for example, may include dispersing such the metal or the metal compound, the composite, or the like in a solvent, coating a conductive carbon material such as carbon paper with the resulting dispersion, and heating the resultant.

A fluorine-containing compound such as polytetrafluoroethylene (PTFE), tetrafluoroethylene oligomer (TFEO), graphite fluoride ((CF)n), pitch fluoride (FP), and a perfluorocarbon sulfonic acid polymer (Nafion or the like) may be mixed in the anode 13. Such a compound is used as a water repellent agent, and enhances the electrochemical reaction efficiency.

The fluorine-containing compound can also be used as a binder in formation of a second electrode. Accordingly, when the composite is formed, the fluorine-containing compound may be further mixed with at least any of a metal and a metal compound, and a conductive carbon material. Alternatively, a conductive carbon material may be coated with a mixture of the composite with the fluorine-containing compound, and the resultant may be heated, thereby performing supporting on the conductive carbon material.

(Third Catalyst)

The first electrochemical cell 11 may comprise a third catalyst that catalyzes a reaction for production of a carbonate compound from carbon monoxide and the alcohol-based compound (1), in the second electrochemical compartment 16. The third catalyst is preferably contained in the filling liquid with which the second electrochemical compartment 16 is filled (the alcohol-based compound (1), or the mixed liquid of the alcohol-based compound (1) with the solvent). The third catalyst may also be supported on the anode 13 and thus contained in the anode 13.

The third catalyst is preferably a redox catalyst. In the present specification, the redox catalyst may be a compound whose oxidized state can be reversibly changed, and examples include a metal compound containing at least one active metal, an organic compound, and halogen. The redox catalyst exhibits oxidation-reduction properties, and therefore not only the redox catalyst catalyzes the reaction of carbon monoxide with the alcohol-based compound (1), but also the redox catalyst itself is reduced, in a region other than the vicinity of the anode. The redox catalyst here reduced can be again oxidized by an electrochemical reaction on the anode, and thus again catalyzes the reaction of carbon monoxide with the alcohol-based compound (1).

The alcohol-based compound (1) with which the second electrochemical compartment is filled is generally reacted with carbon monoxide present in the alcohol-based compound (1) or the mixed liquid of the alcohol-based compound (1) with the solvent, on the anode. When the volume of the alcohol-based compound (1) is large, the reaction of carbon monoxide with the alcohol-based compound (1) is usually limited, with respect to its second reaction, by diffusion of the alcohol-based compound (1) in the vicinity of the anode, causing the entire reaction rate to be lower. However, when the redox catalyst is contained, only the redox catalyst corresponds to a substance diffusing to the anode, and therefore the rate of the reaction in the second electrochemical compartment can be enhanced. In addition, limitations on physical properties of the alcohol-based compound (1) are relaxed, and thus various types of the alcohol-based compounds (1) can be used.

Examples of the active metal contained in the redox catalyst include V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce and Nd. Among them, Pd, Co and Ni are preferable.

Metal-inorganic compounds and metal-organic compounds of these metals can be each used as the metal compound containing the active metal, and specific examples include metal halides, metal oxides, metal hydroxides, metal nitrates, metal sulfates, metal acetates, metal phosphates, metal carbonyls, and organometallic complexes such as metal acetylacetonates.

Specific examples of the metal compound containing the active metal include palladium acetylacetonate ($Pd(OAc)_2$), tetrakis(triphenylphosphine)palladium ($Pd(PPh_3)_4$ complex), tris(2,2'-bipyridine)cobalt ($Co(bpy)_3$ complex), and tris[1,3-bis(4-pyridyl)propane)]cobalt ($Co(bpp)_3$ complex).

Examples of the organic compound used as the redox catalyst include 2,2,6,6-tetramethylpiperidine 1-oxyl (TEMPO).

Examples of the halogen used as the redox catalyst include bromine and iodine.

The third catalyst may be used singly or in combinations of two or more kinds thereof.

The concentration of the third catalyst in the filling liquid with which the second electrochemical compartment 16 is filled is, for example, in the range from 0.001 to 2 mol/L, preferably from 0.001 to 1 mol/L.

(Ion Conducting Membrane)

A solid-state membrane is used as the ion conducting membrane 14, and examples include a cation transport membrane that can transport cation such as proton and an anion transport membrane that can transport anion. In the present embodiment, cation such as proton is generated at the anode 13 as described above, and the cation is sent to the side of the cathode 12 through the ion conducting membrane 13.

Examples of the cation transport membrane preferably include hydrocarbon resin-based poly-sulfonic acids or carboxylic acids, such as polyethylenesulfonic acid, fullerene-crosslinked poly-sulfonic acid and polyacrylic acid, and fluororesin-based sulfonic acids or carboxylic acids, such as perfluoroethylenesulfonic acid. In addition, phosphate glass such as $SiO_2$—$P_2O_5$, heteropolyacids such as tungstosilicic acid and phosphotungstic acid, ceramics such as perovskite type oxide, and the like can also be used.

Examples of the anion transport membrane preferably include resins including a quaternary ammonium salt such as poly(styrylmethyltrimethylammonium chloride), and polyethers.

Among the above cation transport membranes, a perfluoroethylenesulfonic acid resin is preferable. Examples of commercially available products of the perfluoroethylenesulfonic acid resin include Nafion (trademark of Du Pont).

The carbonate compound produced in the second electrochemical compartment 16 may be discharged from a discharge line 20A. The discharge line 20A is configured from, for example, piping or the like connected to the second electrochemical compartment 16. Not only the carbonate compound, but also an unreacted alcohol-based compound (1) is usually discharged from the discharge line 20A. When the solvent, the electrolyte salt, and the like are used, these are also discharged and furthermore a by-product is usually discharged.

Discharging of the carbonate compound from the discharge line 20A is not particularly limited, and may be, for example, performed after a certain amount of the carbonate compound is produced in the second electrochemical compartment 16.

The carbonate compound discharged from the discharge line 20A is sent to the first reactor 21.

The carbonate compound sent to the first reactor 21 is discharged from the discharge line 20A, together with the unreacted alcohol-based compound (1), the solvent, the by-product, the electrolyte salt, and the like, as described above. Accordingly, the carbonate compound is preferably separated by a separation apparatus not illustrated, and then sent to the first reactor 21.

The carbonate compound is usually in the form of a solid or a liquid at an ordinary temperature and an ordinary pressure, and may be fed from the separation apparatus or the second electrochemical compartment 16 to the first reactor 21 by a liquid feed pump or the like.

The separation apparatus is not limited as long as it can separate the carbonate compound and other compounds, and is preferably a distillation apparatus. A distillation apparatus can be used to thereby easily separate the carbonate compound and the unreacted alcohol-based compound (1) by means of the difference in boiling point therebetween. When the solvent and the by-product are contained, not only separation of the carbonate compound and the unreacted alcohol-based compound (1), but also separation of the carbonate compound and the solvent may be conducted. When the by-product is contained, separation of the carbonate compound and the by-product may also be conducted.

The carbonate compound separated may be then sent to the first reactor 21. In addition, the unreacted alcohol-based compound (1), or the unreacted alcohol-based compound (1) and the solvent, separated from the carbonate compound, may be returned from the separation apparatus to the second electrochemical compartment 16, and recycled in an electrochemical reaction in the second electrochemical compartment 16. When the carbonate compound is in the form of a solid at an ordinary temperature and an ordinary pressure, a known powder feed system that can transport the carbonate compound purified and then formed into a powder may be used.

[First Reactor]

In the first reactor 21, a step of synthesizing a predetermined product by a dealcoholization reaction of the carbonate compound (second step) is performed. The product obtained by the dealcoholization reaction of the carbonate compound in the second step may be referred to as a "first product", hereinafter.

The dealcoholization reaction of the carbonate compound, performed in the first reactor 21, is preferably a dealcoholization condensation reaction where dealcoholization is conducted and a condensation reaction is also conducted. Specifically, such a reaction is a reaction in which a compound such as an amine-based compound and/or an alcohol-based compound is added with the alcohol-based compound (1) from the carbonate compound being eliminated.

The amine-based compound added in the first reactor 21 (second step) is a compound having at least one amino group. The alcohol-based compound added in the first reactor 21 (second step) is a compound which has at least one hydroxyl group and which has a structure different from that of the alcohol-based compound (1) synthesized together with carbon monoxide in the first electrochemical cell 11 (first step), and may be referred to as an "alcohol-based compound (2)" hereinafter, for convenience.

The amine-based compound and the alcohol-based compound (2) used in the second step may be fed, for example, through the raw material feed port 18B connected to the first reactor 21, towards the reactor 21.

The amine-based compound and the alcohol-based compound (2) used in the dealcoholization condensation reaction in the second step (namely, first reactor 21) may be an amine-based compound having about 1 to 30 carbon atoms and an alcohol-based compound having about 1 to 30 carbon atoms, respectively, and are preferably a diol-based compound and a diamine-based compound, respectively.

Specific examples of the diol-based compound include a compound represented by the following formula (2).

$$OH—R^1—OH \quad (2)$$

In the formula (2), $R^1$ represents an organic group having 1 to 30 carbon atoms.

In the formula (2), the number of carbon atoms in $R^1$ is preferably 2 to 25, more preferably 3 to 23, further preferably 4 to 21. Examples of the organic group represented by $R^1$ include a divalent hydrocarbon group, and more specific examples thereof include a divalent saturated aliphatic hydrocarbon group, a divalent unsaturated hydrocarbon group and a divalent aromatic hydrocarbon group.

The organic group represented by $R^1$ may also be a hydrocarbon group having a hetero atom, and specific examples include a divalent saturated aliphatic hydrocarbon group having a hetero atom, a divalent unsaturated hydrocarbon group having a hetero atom and a divalent aromatic hydrocarbon group having a hetero atom.

The divalent saturated aliphatic hydrocarbon group or the divalent unsaturated hydrocarbon group may be linear, or may have a branched structure or a cyclic structure.

Examples of the hetero atom include a nitrogen atom, an oxygen atom, a sulfur atom, a phosphorus atom and a halogen atom, and among them, an oxygen atom is preferable and an oxygen atom of an ether bond is preferable.

Among the above, the organic group represented by $R^1$ is preferably a divalent saturated aliphatic hydrocarbon group, a divalent saturated aliphatic hydrocarbon group having a hetero atom, a divalent aromatic hydrocarbon group, or a divalent aromatic hydrocarbon group having a hetero atom. The divalent saturated aliphatic hydrocarbon group having a hetero atom is more preferably a divalent saturated aliphatic hydrocarbon group having an ether bond, and the divalent aromatic hydrocarbon group having a hetero atom is more preferably a divalent aromatic hydrocarbon group having an ether bond.

Examples of the diol compound include alkane diol, polyalkylene glycol, and a bisphenol-based compound.

Examples of the alkane diol preferably include an alkane diol having 2 to 10 carbon atoms, more preferably include an alkane diol having 3 to 6 carbon atoms. Specific examples include linear alkane diols such as ethylene glycol, 1,3-propanediol, 1,2-propanediol, 1,3-butanediol, 1,4-butanediol, 2,3-butanediol, 1,5-pentanediol, 1,2-pentanediol, 1,3-pentanediol, 1,4-pentanediol, 1,5-pentanediol, 1,4-hexanediol, 1,6-hexanediol, 1,4-heptanediol, 1,7-heptanediol, 1,4-octanediol, 1,8-octanediol, 1,4-nonanediol, 1,9-nonanediol, 1,4-decanediol and 1,10-decanediol, branched alkane diols such as 2-methyl-1,3-propanediol, 3-methyl-1,5-pentanediol, 2-methyl-1,8-octanediol and 2,2-diethyl-1,3-propanediol, and aliphatic diols each having a cycloalkyl group, such as 1,2-cyclohexanediol, 1,4-cyclohexanediol, 1,2-cyclohexanedimethanol, 1,4-cyclohexanedimethanol, 1,3-cyclobutanediol, 2,2,4,4,-tetramethyl-1,3-cyclobutanediol and hydrogenated bisphenol A. Among them, linear alkane diols are preferable, and linear alkane diols having 3 to 6 carbon atoms are more preferable.

Examples of the polyalkylene glycol include diethylene glycol, polyethylene glycol, dipropylene glycol, polypropylene glycol and polytetramethylene glycol.

The bisphenol-based compound is not particularly limited as long as it is a compound having two hydroxy phenyl groups, and examples preferably include a compound represented by the following formula (2-1).

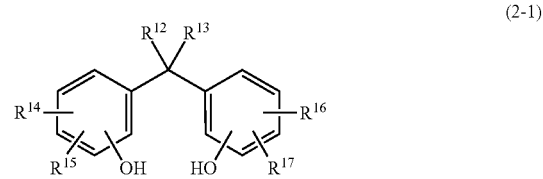

(2-1)

In the formula (2-1), $R^{12}$ and $R^{13}$ each independently represent a hydrogen atom, a methyl group, an ethyl group or a phenyl group, or $R^{12}$ and $R^{13}$ may be bound to form a cycloalkane structure. The cycloalkane structure is a cycloalkane structure in which the number of carbon atoms forming a ring is 5 to 8, preferably the number of carbon atoms is 6, and any hydrogen atom of the cycloalkane may be substituted with a methyl group.

$R^{14}$, $R^{15}$, $R^{16}$, and $R^{17}$ each independently represent, for example, a hydrogen atom, an alkyl group having 1 to 8 carbon atoms, or an alkoxy group having 1 to 4 carbon atoms. The alkyl group having 1 to 8 carbon atoms may be linear, or may have a branched structure or a cyclic structure. The alkyl group having 1 to 8 carbon atoms is preferably an alkyl group having 1 to 4 carbon atoms, and examples include a methyl group, an ethyl group, a n-propyl group, an isopropyl group, a n-butyl group, a t-butyl group, a sec-butyl group and an isobutyl group. Examples of the alkoxy group having 1 to 4 carbon atoms preferably include an alkoxy group having 1 or 2 carbon atoms, and specific examples include a methoxy group and an ethoxy group.

Among the above, a bisphenol compound is more preferable where both $R^{12}$ and $R^{13}$ represent a hydrogen atom or a methyl group, and $R^{14}$, $R^{15}$, $R^{16}$, and $R^{17}$ each independently represent any selected from the group consisting of a hydrogen atom, an alkyl group having 1 to 4 carbon atoms and an alkoxy group having 1 to 2 carbon atoms.

Specific suitable examples of the diol compound include 1,4-butanediol, bisphenol A, m,m'-bisguaiacol represented by the following formula (2-2), isosorbide, and decanediol.

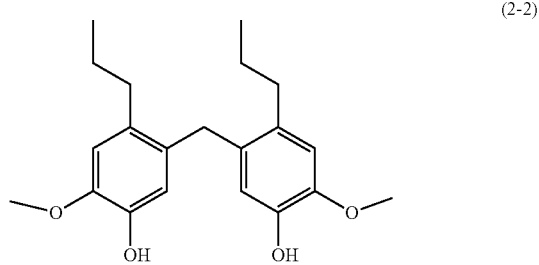

(2-2)

Specific examples of the diamine-based compound include a compound represented by the following formula (3).

$H_2N—R^2—NH_2$ (3)

In the formula (3), $R^2$ represents an organic group having 1 to 30 carbon atoms.

In the formula (3), the number of carbon atoms in $R^2$ is preferably 2 to 25, more preferably 3 to 20, further preferably 4 to 12.

Examples of the organic group represented by $R^2$ include a divalent hydrocarbon group, and more specific examples thereof include a divalent saturated aliphatic hydrocarbon group, a divalent unsaturated hydrocarbon group and a divalent aromatic hydrocarbon group.

The organic group represented by $R^2$ may also be a hydrocarbon group having a hetero atom, and specific examples include a divalent saturated aliphatic hydrocarbon group having a hetero atom, a divalent unsaturated hydrocarbon group having a hetero atom and a divalent aromatic hydrocarbon group having a hetero atom.

The divalent saturated aliphatic hydrocarbon group or the divalent unsaturated hydrocarbon group may be linear, or may have a branched structure or a cyclic structure.

Examples of the hetero atom include a nitrogen atom, an oxygen atom, a sulfur atom, a phosphorus atom and a halogen atom, and among them, an oxygen atom is preferable and an oxygen atom of an ether bond is preferable.

Among the above, the organic group represented by $R^2$ is preferably a divalent saturated aliphatic hydrocarbon group.

Specific examples of the diamine compound include alkanediamine. More specific examples include linear alkanediamines such as 1,2-ethanediamine, 1,3-propanediamine, 1,4-butanediamine, 1,4-pentanediamine, 1,5-pentanediamine, 1,4-hexanediamine, 1,6-hexanediamine, 1,4-heptanediamine, 1,7-heptanediamine, 1,4-octanediamine, 1,8-octanediamine, 1,4-nonanediamine, 1,9-nonanediamine, 1,4-decanediamine, 1,10-decanediamine, 1,4-undecanediamine, 1,11-undecanediamine, 1,4-dodecanediamine and 1,12-dodecanediamine, branched alkanediamines such as 2-methyl-1,5-pentanediamine, 3-methyl-1,5-pentanediamine, 2-methyl-1,8-octanediamine, 2,2,4-trimethyl-1,6-hexanediamine, 2,4,4-trimethyl-1,6-hexanediamine and 5-methyl-1,9-nonanediamine, and cyclic alkanediamines such as 1,4-cyclohexanediamine. These may be used singly or in combinations of two or more kinds thereof.

A compound having a cyclic ether structure, such as isoidide diamine, other than the alkanediamine may be adopted.

Among them, linear alkanediamines are preferable, and linear alkanediamines having 4 to 12 carbon atoms are more preferable.

The amine-based compound and the alcohol-based compound (2) used in the dealcoholization condensation reaction in the second step (namely, first reactor 21) may be a compound other than the diol-based compound and the diamine-based compound.

Specific examples include biscatechol-based compounds such as 4,4'-methylenebiscatechol, 4,4'-isopropylidenebiscatechol, 4,4'-methylenebis(propylcatechol) and 4,4'-isopropylidenebis(propylcatechol), and alcohol-based compounds (2) having three or more hydroxyl groups, such as diglycerol.

Besides the above, a saturated alkyl alcohol, an unsaturated alkyl alcohol, a saturated alkylamine, an unsaturated alkylamine, and the like may be adopted. These may have one hydroxyl group or amino group, or may have three or more hydroxyl groups or amino groups.

When the diol-based compound is used in the second step, the first product produced from the carbonate compound and the diol-based compound is, for example, a compound obtained by addition condensation of the carbonate compound to each of two hydroxy groups of the diol-based compound. Specifically, for example, a dicarbonate compound represented by the following formula (4-1) is synthesized as the first product from the carbonate compound and the diol-based compound represented by the formula (2).

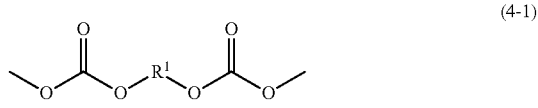

(4-1)

In the formula (4-1), $R^1$ has the same meaning as above.

When the diamine-based compound is used, the first product produced from the carbonate compound and the diamine-based compound in the second step is, for example, a compound obtained by addition condensation of the carbonate compound to each of two amino groups of the diamine-based compound. Specifically, for example, a dicarbamate compound represented by the following formula (5-1) is synthesized as the first product from the carbonate compound and the diamine-based compound represented by the formula (3).

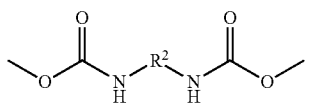

(5-1)

In the formula (5-1), $R^2$ has the same meaning as above.

In the first reactor 21 (second step), the carbonate compound, and at least one selected from the group consisting of the diol-based compound represented by the formula (2) and the diamine-based compound represented by the formula (3) may be polycondensated to synthesize a polymer having at least any of repeating units represented by the following formula (4-2) and formula (5-2), as the first product. In the present embodiment, a useful polymer can be produced from carbon monoxide in a small number of steps.

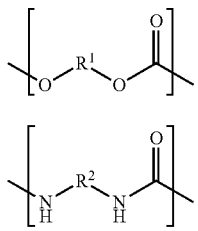

(4-2)

(5-2)

In the formula (4-2) and the formula (5-2), $R^1$ and $R^2$ each have the same meaning as above.

The polymer obtained in the present embodiment is polycarbonate, polyurethane, or the like. In the present invention, polycarbonate and polyurethane can be produced even without any highly toxic raw materials such as phosgene and diisocyanate.

More specifically, a polycarbonate represented by the following formula (4-3) is obtained in the second step by polycondensation of the carbonate compound and the diol-based compound represented by the formula (2). For example, a polyurethane represented by the following formula (5-3) is obtained by polycondensation of the carbonate compound and the diamine-based compound represented by the formula (3).

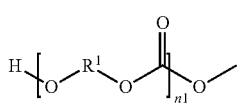

(4-3)

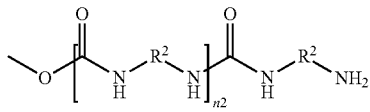

(5-3)

In the formulae (4-3) and (5-3), $R^1$ and $R^2$ each have the same meaning as described above; and n1 and n2 each independently represent an integer of 2 or more.

Here, n1 and n2 each independently preferably represent 10 or more, more preferably 50 or more, and preferably 5000 or less, more preferably 2000 or less.

The amount of the carbonate compound to be used relative to at least one selected from the group consisting of the amine-based compound and the alcohol-based compound (2) in the first reactor 21 varies depending on a target product. For example, when the target product is a dicarbonate compound or a dicarbamate compound as described above, the amount of the carbonate compound to be loaded with respect to the amount of at least one selected from the group consisting of the diamine-based compound and the diol-based compound may be excessive at a molar ratio, and is preferably 1.9 or more and 50 or less, more preferably 2 or more and 12 or less.

As described above, when the target product produced in the first reactor 21 is a polymer, the amount of the carbonate compound to be loaded with respect to the amount of at least one selected from the group consisting of the diamine-based compound and the diol-based compound is preferably close to 1 at a molar ratio is, for example, 0.5 or more and 2 or less, more preferably 0.95 or more and 1.05 or less.

In the second step, the reaction of the carbonate compound and at least any selected from the group consisting of the amine-based compound and the alcohol-based compound (2) may be performed in the presence of a catalyst.

Examples of the catalyst used in the reaction of the carbonate compound and the amine-based compound include a Lewis acid catalyst, a lead, titanium or zirconium-based catalyst, a hydroxide or alcoholate catalyst of an alkali metal or an alkali earth metal, an amidine compound, and metal carbonates such as sodium carbonate and potassium carbonate. Among them, an amidine compound is preferable.

Examples of the amidine compound include a cyclic amidine compound in which at least one nitrogen atom forms a part of an alicyclic or heterocyclic ring. Suitable examples of the cyclic amidine compound include a compound in which a nitrogen atom forms a part of a fused ring made of a 6-membered ring and a 5-membered ring, a 6-membered ring and a 7-membered ring, or two 6-membered rings. Specific examples of the cyclic amidine compound include 1,5-diazabicyclo[4.3.0]non-5-ene (DBN), 1,8-diazabicyclo[5.4.0]undec-7-ene (DBU), and 1,5,7-triazabicyclo[4.4.0]dec-5-ene (TBD), and among them, TBD is preferable.

A catalyst used for common transesterification can be used as the catalyst used in the reaction of the carbonate compound and the alcohol-based compound (2), and examples include a metal catalyst and a nitrogen-containing basic compound. Preferable examples of the metal catalyst include a tin compound such as dibutyltin oxide. Examples of the nitrogen-containing basic compound include pyridines such as 2-aminopyridine, 4-aminopyridine, 4-dimethylaminopyridine and 4-diethylaminopyridine, and among them, 4-dimethylaminopyridine is preferable.

The amount of the catalyst to be used is, for example, 0.001 or more and 0.4 or less, preferably 0.005 or more and 0.2 or less at a molar ratio, relative to at least one selected from the group consisting of the amine-based compound and the alcohol-based compound (2).

The reaction temperature in the reaction for production of the first product from the carbonate compound in the first reactor 21 (second step) may be, for example, about 25° C. or more and 400° C. or less, and is preferably 70° C. or more and 180° C. or less.

The reaction temperature in the first reactor 21 (second step) may be stepwisely increased. For example, when the diol-based compound is used as a raw material, a first step reaction may be performed at about 100° C. or more and 150° C. or less, and a second step reaction may be performed at a temperature higher than the temperature at the first step reaction by about 20 to 60° C. The reaction is thus stepwise performed, thereby allowing a polymer or the like to be easily produced.

In the first reactor 21, a continuous reaction may be performed or a batch reaction may be performed. When a batch reaction is performed, the reaction time in the first reactor 21 is not particularly limited, and is about 30 minutes or more and 60 hours or less.

In the first reactor 21 (second step), while the first product being synthesized, alcohol-based compound (1) is eliminated. Accordingly, the alcohol-based compound (1) and the first product are present in a liquid reactant in the first reactor 21 in a mixed state. In addition, not only the alcohol-based compound (1) and the first product, but also the catalyst, the by-product, and the like are usually present in the first reactor 21.

Therefore, the alcohol-based compound (1) eliminated in the first reactor 21 may be separated from the first product, and furthermore the catalyst, the by-product, and the like. The alcohol-based compound (1) separated is returned to a region at the side of the anode (namely, second electrochemical compartment 16) of the first electrochemical cell 11 through a feed pathway 20B. Herein, the alcohol-based compound (1) separated can be stored in another container once, and may be fed to the second electrochemical compartment 16 through the feed pathway 20B, when required. The feed pathway 20B is, for example, piping that connects the region at the side of the anode of the first electrochemical cell 11 to the first reactor 21 or such another container described above. The alcohol-based compound (1) separated may be returned to the second electrochemical compartment 16 by a liquid feed pump or the like.

Separation of the alcohol-based compound (1) and the first product may be performed in the first reactor 21, or may be performed in a separation apparatus provided separately from the first reactor 21. Examples of the method for separating the alcohol-based compound (1) include a method in which the alcohol-based compound is removed by distillation or the like.

When the separation is performed in the first reactor 21, the alcohol-based compound (1) may be removed by distillation from the first reactor 21 after the carbonate compound fed to the first reactor 21 is converted into the first product at a predetermined ratio or more.

The alcohol-based compound (1) eliminated may also be removed by distillation while the reaction for production of the first product being allowed to progress (namely, the dealcoholization reaction being allowed to progress). In this case, the alcohol-based compound (1) eliminated may be removed by distillation while the internal temperature of the first reactor 21 being set to a temperature equal to or higher than the boiling point of the alcohol-based compound (1) to allow the dealcoholization reaction to progress. The alcohol-based compound (1) may be removed by distillation together with the solvent, other by-product, and the like, and in such a case, an obtained product by distillation may be further purified. Herein, the boiling point of the alcohol-based compound (1) means the boiling point under the internal pressure of the first reactor 21, and therefore means the boiling point of the alcohol-based compound (1) under reduced pressure when the pressure of the inside of the first reactor 21 is reduced.

When the separation is performed in a separation apparatus (not illustrated) provided separately from the first reactor 21, a distiller or the like may be used as the separation apparatus. When the separation apparatus is used, for example, the liquid reactant may be sent from the first reactor 21 to the separation apparatus, and the alcohol-based compound (1) separated in the separation apparatus may be sent through the feed pathway 20B to the region at the side of the anode (namely, second electrochemical compartment 16).

Furthermore, the method for separating the alcohol-based compound (1) may be a method in which the alcohol-based compound is separated by solid-liquid separation when the alcohol-based compound (1) is in the form of a liquid and the first product is in the form of a solid. Here, the first product may be precipitated by addition of a poor solvent or the like of the first product. The solid-liquid separation may be performed by centrifugation or the like, or may be performed by filtration or the like. The alcohol-based compound (1) may be separated by liquid-liquid extraction or the like by means of the difference in solubility. The first product may be appropriately purified by each of the above operations.

The alcohol-based compound (1) separated may be fed to the second electrochemical compartment 16 by a liquid feed pump or the like.

The alcohol-based compound (1) eliminated in the first reactor 21 is sent to the region at the side of the anode (namely, second electrochemical compartment 16) of the first electrochemical cell 11, and recycled for synthesis of the carbonate compound in the second electrochemical compartment 16. That is, the alcohol-based compound (1) is synthesized by an electrochemical reaction with carbon monoxide fed from the gas feed line 17 and converted into the carbonate compound, in the second electrochemical compartment 16 according to the same method as above.

As described above, in the present embodiment, a circulation line 20 is formed from the discharge line 20A and the feed pathway 20B in the synthesis system 10. The compound (carbonate compound) produced at the side of the anode of the first electrochemical cell 11 is then fed through the circulation line 20 to the first reactor 21, and the compound (alcohol-based compound) eliminated in the first reactor 21 is fed to the side of the anode (second electrochemical compartment 16) of the electrochemical cell 11. That is, the respective compounds produced in the first reactor 21 and the second electrochemical compartment 16 are circulated by the circulation line 20.

Such a circulation line 20 can be formed to thereby allow the synthesis system of the present embodiment to easily circulate the compounds produced in the first reactor 21 and the second electrochemical compartment 16, and to efficiently perform the first and second steps.

Second Embodiment

Next, a second embodiment of the present invention will be described.

A synthesis system 30 according to the second embodiment of the present invention comprises a second reactor 22 that is a separate reactor from the first reactor 21, in addition to the configuration of the first embodiment, as illustrated in FIG. 2. Hereinafter, the synthesis system of the second embodiment will be described with respect to differences from the synthesis system of the first embodiment.

While the dealcoholization reaction of the carbonate compound is performed in only the first reactor 21 in the first embodiment as described above, it is performed in both the first and second reactors 21 and 22 in the present embodiment.

In the first reactor 21, the first product is produced while the alcohol-based compound (1) being eliminated, as in the first embodiment, and the alcohol-based compound eliminated is returned to the region at the side of the anode (namely, second electrochemical compartment 16) of the first electrochemical cell 11 through the feed pathway 20B. As described above, separation of the alcohol-based compound (1) and the first product may be performed in the first reactor 21, or may be performed in a separation apparatus (not illustrated) that is a separated apparatus from the first reactor 21.

In the present embodiment, the first product produced in the first reactor 21 is sent to the second reactor 22, and further subjected to a dealcoholization reaction in the second reactor 22, resulting in synthesis of the second product (third step). The first product may be sent to the second reactor 22 through, for example, a connection pathway 20E. With respect to the first product, when the above separation apparatus is provided, the first product separated from the alcohol-based compound (1) may be sent from the separation apparatus through the connection pathway 20E to the second reactor 22. The connection pathway 20E may be, for example, piping, or may be a known powder feed system that can transport the first product formed into a powder when the first product is in the form of a solid. The first product may be taken out from the first reactor 21, the separation apparatus, and the like without any connection pathway 20E provided, and the first product may be loaded to the second reactor 22.

In the present embodiment, the two reactors 21 and 22 are used to produce a target product (second product), and therefore the target product is more efficiently easily synthesized by setting respective different reaction conditions in the reactors 21 and 22. Specifically, the target product can be more efficiently synthesized by using different catalysts from each other and/or setting different reaction temperatures from each other in the second step and the third step.

Also in the second embodiment, a reaction is performed in which, while the alcohol-based compound (1) being eliminated from the carbonate compound, the compound such as the amine-based compound or the alcohol-based compound is added to provide the first product, in the second step (first reactor 21).

In addition, a reaction is performed in which, while the alcohol-based compound (1) being eliminated from the first product, the compound such as the amine-based compound or the alcohol-based compound is added to provide the second product, in the third step (second reactor 22). In this case, at least any of the diol-based compound and the diamine-based compound is fed to the second reactor 22 through, for example, a raw material feed port 18C, as in the first reactor 21.

A polymer of the first product, however, may be produced as the second product by polymerizing the first product without feeding any diol-based compound and any diamine-based compound.

In the second embodiment, the target product (namely, second product) is preferably a polymer. Therefore, the first product is preferably a precursor compound of the polymer, specifically preferably a dicarbamate compound or a dicarbonate compound.

More specifically, it is preferable in the first reactor 21 (second step) that the dicarbonate compound represented by the formula (4-1) or the dicarbamate compound represented by the formula (5-1) be produced as the first product from any of the diamine-based compound and the diol-based compound, and the carbonate compound.

The amount of the carbonate compound here to be used relative to at least one selected from the group consisting of the amine-based compound and the alcohol-based compound (2) is as described in the first embodiment.

On the other hand, in the second reactor 22 (third step), a polymer having at least any of the repeating units represented by the formula (4-2) and the formula (5-2) may be synthesized as the second product by polycondensation of the first product and at least one of the diol-based compound and the diamine-based compound fed to the second reactor 22. In this case, the amount of at least one of the diol-based compound and the diamine-based compound relative to the first product is preferably close to 1 at a molar ratio, and is, for example, 0.5 or more and 2 or less, more preferably 0.95 or more and 1.05 or less.

When the first product is produced from the diol-based compound and the carbonate compound and any polycarbonate is obtained as the target product (second product), a polymer having the repeating unit represented by the formula (4-2) may be produced as the second product by polycondensation of the first product such as the dicarbonate compound without feeding any diol-based compound and any diamine-based compound to the second reactor 22.

Specific examples of the polymer obtained as the second product include the polycarbonate represented by the formula (4-3) and the polyurethane represented by the formula (5-3).

Polyurethane having both the repeating units represented by the formula (4-2) and the formula (5-2) may also be included. Such polyurethane having both the repeating units can be synthesized by, for example, producing the dicarbonate compound as the first product and also feeding the diamine-based compound to the second reactor 22 to polycondensate the dicarbonate compound and the diamine-based compound in the second reactor 22 (third step). Such polyurethane usually has a repeating unit represented by the following formula (4-4).

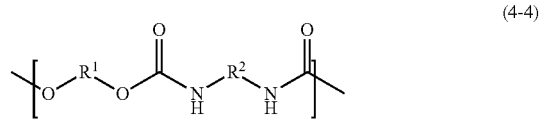

(4-4)

In the formula (4-4), $R^1$ and $R^2$ each have the same meaning as above.

Also in the second embodiment, the reaction of the carbonate compound and at least any selected from the group consisting of the amine-based compound and the alcohol-based compound (2) may be performed in the presence of a catalyst in the second step. The reaction of the first product and at least any selected from the group consisting of the amine-based compound and the alcohol-based compound (2), or the polymerization reaction of the first product may be performed in the presence of a catalyst, in the third step.

The respective catalysts used in the second step and the third step may be appropriately selected from the group consisting of those listed as the catalyst used in the second step of the first embodiment.

The amount of the catalyst used in the second step is, for example, 0.001 or more and 0.75 or less, preferably 0.005 or more and 0.2 or less at a molar ratio relative to the amine-based compound or the alcohol-based compound (2).

On the other hand, the amount of the catalyst used in the third step is, for example, 0.001 or more and 0.75 or less, preferably 0.005 or more and 0.2 or less at a molar ratio relative to the first product.

A polycondensation reaction in synthesis of a polymer is generally often needed to be increased in the reaction temperature as compared with a reaction in which a carbonate compound and a diol-based compound or a diamine-based compound are reacted to synthesize a dicarbamate compound, a dicarbonate compound, or the like. In addition, the change of a catalyst easily allows for an enhancement in the reactivity in each reaction, easily resulting in an enhancement in the yield or the like.

Accordingly, in the present embodiment, the target product being a polymer can be more efficiently synthesized by performing the step of producing the first product (for example, the compound represented by the formula (4-1) or the formula (5-1)) by the reaction of the carbonate compound and the diol-based compound or the diamine-based compound, and the step of producing the polymer (for example, polymer having at least any of the repeating units represented by the formula (4-2) and the formula (5-2)) by polycondensation in the separate reactors (first and second reactors 21 and 22), as described above.

In the second embodiment, the reaction temperature in the reaction for production of the first product from the carbonate compound in the first reactor 21 (second step) may be, for example, about 25° C. or more and 400° C. or less, and is preferably 70° C. or more and 180° C. or less.

Also in the second embodiment, a continuous reaction may be performed or a batch reaction may be performed in the first reactor 21. When a batch reaction is performed, the reaction time in the first reactor 21 is not particularly limited, and is about 30 minutes or more and 60 hours or less.

In the second reactor 22 (third step), the reaction temperature in the reaction for production of the second product from the first product is not particularly limited, and it is preferably higher than the reaction temperature in the first reactor 21 (second step). Specifically, the reaction temperature may be higher by about 30 to 100° C. A specific reaction temperature is, for example, 100° C. or more and 250° C. or less, preferably 140° C. or more and 240° C. or less.

In the second reactor 22, a continuous reaction may be performed or a batch reaction may be performed. When a batch reaction is performed, the reaction time in the first reactor 21 is not particularly limited, and is about 30 minutes or more and 60 hours or less, preferably 1 hour or more and 12 hours or less.

In the second reactor 22 (third step) of the second embodiment, the alcohol-based compound (1) is eliminated while the second product being synthesized. Accordingly, at least the alcohol-based compound (1) and the second product in a mixed state are present in a liquid reactant in the second reactor 22. In addition, not only the alcohol-based compound (1) and the second product, but also the catalyst, the by-product, the first product serving as a raw material, and the like are usually present in the second reactor 22. Therefore, the alcohol-based compound (1) eliminated in the second reactor 22 may be separated from the second product, and furthermore the catalyst, the by-product, the first product, and the like. The alcohol-based compound (1) separated is returned to a region at the side of the anode (namely, second electrochemical compartment 16) of the first electrochemical cell 11 through a feed pathway 20C. Herein, the alcohol-based compound (1) separated can be stored in another container once, and may be fed to the second electrochemical compartment 16 through the feed pathway 20C, when required. The feed pathway 20C is, for example, piping that connects the region at the side of the anode of the first electrochemical cell 11 to the first reactor 22 or such another container described above. The alcohol-based compound (1) separated may be returned to the second electrochemical compartment 16 by a liquid feed pump or the like.

Separation of the alcohol-based compound (1) and the second product may be performed in the second reactor 22, or may be performed in a separation apparatus provided separately from the second reactor 22. Examples of the method for separating the alcohol-based compound (1) include a method in which the alcohol-based compound is removed by distillation or the like.

When the separation is performed in the second reactor 22, the alcohol-based compound (1) may be removed by distillation from the first reactor 21 after the first product fed to the second reactor 22 is converted into the second product at a predetermined ratio or more.

The alcohol-based compound (1) eliminated may be removed by distillation while the reaction for production of the second product being allowed to progress (namely, the dealcoholization reaction being allowed to progress). In this case, the alcohol-based compound (1) eliminated may be removed by distillation while the internal temperature (reaction temperature) of the second reactor 22 being set to a temperature equal to or higher than the boiling point of the alcohol-based compound (1) to allow the dealcoholization reaction to progress. Here, the boiling point of the alcohol-based compound (1) may be decreased by reducing the pressure of the inside of the second reactor 22, to thereby allow the alcohol-based compound (1) to be easily removed by distillation. The alcohol-based compound (1) may be removed by distillation together with the solvent, other by-product, and the like, and in such a case, an obtained product by distillation may be further purified.

When the separation is performed in a separation apparatus (not illustrated) provided separately from the second reactor 22, a distiller or the like may be used as the separation apparatus. When the separation apparatus provided separately from the first reactor 22 is used, for example, the liquid reactant may be sent from the first reactor 22 to the separation apparatus, and the alcohol-based compound (1) separated in the separation apparatus may be sent through the feed pathway 20C to the region at the side of the anode (namely, second electrochemical compartment 16).

Furthermore, the method for separating the alcohol-based compound (1) and the second product may be a method in which the alcohol-based compound is separated from the second product by solid-liquid separation when the alcohol-based compound (1) is in the form of a liquid and the second product is in the form of a solid. Here, the second product may be precipitated by addition of a poor solvent or the like of the second product. The solid-liquid separation may be performed by centrifugation or may be performed by filtration. The alcohol-based compound (1) may be separated by liquid-liquid extraction or the like by means of the difference in solubility. The second product may be appropriately purified by each of the above operations.

In the present embodiment, the alcohol-based compound (1) eliminated in the first and second reactors 21 and 22 is sent to the region at the side of the anode (namely, second electrochemical compartment 16) of the first electrochemical cell 11, and recycled for synthesis of the carbonate compound.

Thus, a circulation line is formed from the discharge line 20A and the feed pathway 20B, as in the first embodiment, and another circulation line is further formed from the feed pathway 20C, in the synthesis system 30 of the present embodiment. The compound (carbonate compound) produced at the side of the anode of the first electrochemical cell 11 is then converted into the respective target products in the first reactor 21 and furthermore the second reactor 22 through the circulation line, and the compound (alcohol-based compound) eliminated in the course of such conversion is fed to the first electrochemical compartment 16 (namely, the region at the side of the anode). That is, the respective compounds produced in the first and second reactors 21 and 22 and the second electrochemical compartment 16 are circulated by the circulation line.

Such a circulation line can be formed to thereby allow the synthesis system of the present embodiment to easily circulate the compounds produced in the first reactor 21 and the second electrochemical compartment 16, and to efficiently perform synthesis of the target products.

Third Embodiment

Next, a third embodiment of the present invention will be described.

While carbon monoxide used as a raw material is fed to the side of the anode of the first electrochemical cell 11 from one other than the first electrochemical cell 11 in the first embodiment, carbon monoxide produced at the side of the cathode of the first electrochemical cell 11 is fed to the side of the anode of the first electrochemical cell 11 in the third embodiment. Hereinafter, a synthesis system 35 according to the third embodiment of the present invention will be described with respect to differences from the synthesis system of the first embodiment, with reference to FIG. 3.

The synthesis system 35 of the third embodiment comprises a first connecting path 36. The first connecting path 36 connects the first electrochemical compartment 15 and the second electrochemical compartment 16, and feeds carbon monoxide produced in the first electrochemical compartment 15, to the second electrochemical compartment 16. That is, the first connecting path 36 in the present embodiment is a first gas feed line that feeds carbon monoxide to the side of the anode of the first electrochemical cell 11.

The first connecting path 36 is, for instance, a conducting pipe or the like which connects the first electrochemical compartment 15 and the second electrochemical compartment 16, and it may have a flow rate adjusting mechanism or the like provided so as to adjust a flow rate and the like. In addition, a non-return valve or the like may be attached to the conducting pipe, so that the gas is sent from the first electrochemical compartment 15 to the second electrochemical compartment 16 through the first connecting path 36 but the gas is not sent in the reverse direction.

A second gas feed line 25 is connected to the first electrochemical compartment 15 of the first electrochemical cell 11, and carbon dioxide is fed through the second gas feed line 25. In the first electrochemical cell 11, carbon dioxide is first fed to the first electrochemical compartment 15, and carbon dioxide fed is reduced on the cathode 12, to produce carbon monoxide. The catalyst for reduction (first catalyst) contained in the cathode 12 may be any catalyst for reduction as long as such a catalyst for reduction can reduce carbon dioxide to carbon monoxide, and may be appropriately selected from the group consisting of the catalysts described in the first embodiment, and used.

Carbon monoxide produced in the first electrochemical compartment 15 passes through the first connecting path 36 in the form of gas and is allowed to flow out into the second electrochemical compartment 16. Here, carbon monoxide may be allowed to flow out into the second electrochemical compartment 16 together with unreacted carbon dioxide in the first electrochemical compartment 15.

When the first electrochemical compartment 15 is not filled with a filling liquid such as an electrolyte solution, carbon monoxide produced may be sequentially mixed with unreacted carbon dioxide in a gas phase, and allowed to pass through the first connecting path 36 and flow out into the second electrochemical compartment 16 as it is. A reduction reaction of carbon dioxide produces not only carbon monoxide, but also water as a by-product. The water produced as a by-product may remain in the electrochemical compartment, and may be discharged when stored in a certain amount. The first electrochemical compartment 15 may be provided with a discharge port for discharging of the water as a by-product.

Also in the above third embodiment, not only the carbonate compound produced in the first electrochemical cell 11 is converted into the first product in the first reactor 21, but also the alcohol-based compound (1) eliminated in the first reactor 21 is recycled in the region at the side of the anode (second electrochemical compartment 16) of the first electrochemical cell 11, and therefore the target product can be efficiently produced.

Furthermore, in the present embodiment, carbon monoxide produced at the cathode 12 of the first electrochemical cell 11 is used, as it is, for production of the carbonate compound at the side of the anode 13. Therefore, there is no need for any carbon monoxide source separately provided, and thus the target product can be efficiently obtained.

Here, the synthesis system of the third embodiment may further comprise a second connecting path 37 that connects the first electrochemical compartment 15 and the second electrochemical compartment 16, in addition to the first connecting path 36, as illustrated in FIG. 4.

The second connecting path 37 is, for instance, a conducting pipe of the like which connects the first electrochemical compartment 15 with the second electrochemical compartment 16, and it may have a flow rate adjusting mechanism or the like provided so as to adjust a flow rate and the like. In addition, a non-return valve or the like may be attached to the conducting pipe, so that gas is sent from the second electrochemical compartment 16 to the first electrochemical compartment 15 but the gas is not sent from in the reverse direction.

In the third synthesis system 35, the second connecting path 37 can be provided to thereby allow unreacted carbon dioxide passing through the first electrochemical compartment 15 and the first connecting path 36 and flowing out into the second electrochemical compartment 16 to further pass through the second electrochemical compartment 16 and the second connecting path 37 and again flow into the first electrochemical compartment 15 in the form of gas. Thus, carbon dioxide can be circulated in a circuit including the first electrochemical compartment 15, the first connecting path 36, the second electrochemical compartment 16, the second connecting path 37 and the first electrochemical compartment 15, and subjected to the reduction reaction on the cathode 12 in the course of such circulation, resulting in an enhancement in the conversion of carbon dioxide into carbon monoxide.

The component passing through the second connecting path 37 and flowing into the first electrochemical compartment 15 may contain not only the above unreacted carbon dioxide, but also unreacted carbon monoxide or the like not subjected to the reaction at the side of the anode, among carbon monoxide produced in the first electrochemical compartment 15 and flowing out into the second electrochemical compartment 16. Carbon monoxide may be circulated in the order of the second electrochemical compartment 16, the second connecting path 37, the first electrochemical compartment 15, the first connecting path 36 and the second electrochemical compartment 16, and subjected to the reaction at the side of the anode in the course of such circulation, as in carbon dioxide. Thus, the conversion rate of carbon monoxide to the carbonate compound is increased.

Fourth Embodiment

Next, a fourth embodiment of the present invention will be described.

While carbon monoxide used as a raw material is fed from one other than the first electrochemical cell 11 to the side of the anode of the first electrochemical cell 11 in the second embodiment, carbon monoxide produced at the side of the cathode of the first electrochemical cell 11 is fed to the side of the anode of the first electrochemical cell 11 in the fourth embodiment. Hereinafter, a synthesis system 40 according to the fourth embodiment of the present invention will be described with respect to differences from the synthesis system of the second embodiment, with reference to FIG. 5.

The synthesis system 40 of the fourth embodiment comprises a first connecting path 36. The first connecting path 36 is the same as the first connecting path in the third embodiment. The second gas feed line 25 is connected to the first electrochemical compartment 15 of the first electrochemical cell 11 as in the third embodiment, and carbon dioxide is fed through the second gas feed line 25. Carbon monoxide is then produced at the side of the cathode of the first electrochemical cell 11 and carbon monoxide is used in production of the carbonate compound at the side of the anode 13, as in the third embodiment. Therefore, in the present embodiment, there is no need for any carbon monoxide source separately provided, as in the third embodiment, and therefore the target product can be efficiently obtained.

Also in the fourth embodiment, not only the carbonate compound produced in the first electrochemical cell 11 is converted into the first product in the first reactor 21, but also the first product is fed to the second reactor 22 and the second product is produced in the second reactor 22. In addition, the alcohol-based compounds eliminated in the first and second reactors 21 and 22 are fed to the region at the side of the anode (second electrochemical compartment 16) of the first electrochemical cell 11, and therefore the target product can be efficiently produced as in the second embodiment.

Also in the fourth embodiment, a second linkage tube (not illustrated) may be provided as in the third embodiment. The second linkage tube can be provided to allow carbon monoxide and carbon dioxide to be circulated in the first electrochemical cell 11, resulting in enhancements in the conversion rate from carbon dioxide to carbon monoxide, and the conversion rate from carbon monoxide to the carbonate compound.

While an aspect in which all carbon monoxide fed to the region at the side of the anode of the electrochemical cell 11 (second electrochemical compartment 16) is fed from the region at the side of the cathode (first electrochemical compartment 15) is illustrated in the third and fourth embodiments, a part of such carbon monoxide may be fed from the first electrochemical compartment 15 and another part thereof may be fed from another carbon monoxide source.

Fifth Embodiment

Next, a fifth embodiment of the present invention will be described.

While carbon monoxide is fed from the carbon monoxide source to the side of the anode of the first electrochemical cell 11 in the first embodiment, an electrochemical cell (also referred to as a "second electrochemical cell Si") different from the first electrochemical cell 11 is provided in a synthesis system 50 of the fifth embodiment and carbon monoxide produced in the second electrochemical cell 51 is fed to the side of the anode of the first electrochemical cell 11, as illustrated in FIG. 6.

Hereinafter, the fifth embodiment will be described with respect to differences from the first embodiment.

As illustrated in FIG. 6, the second electrochemical cell 51 comprises a cathode 52 and an anode 53 therein, as in the first electrochemical cell 11. The second electrochemical cell 51 further comprises an ion conducting membrane 54, and has a two-chamber membrane-type cell-structure where the cell is partitioned by the ion conducting membrane 54 and separated to two chambers, to allow a first electrochemical compartment 55 and a second electrochemical compartment 56 to be formed. The first electrochemical compartment 55 and the second electrochemical compartment 56 are provided with the cathode 52 and the anode 53 disposed therein, respectively, and form a region at the side of the cathode 52 (cathode region) and a region at the side of the anode 53 (anode region), respectively.

The cathode 52 and the anode 53 are, for example, disposed on and jointed to each surface of the ion conducting membrane 53, respectively, and are taken together with the ion conducting membrane 54 to form a membrane-electrode assembly, as illustrated in FIG. 6. A power source 59 is connected to the cathode 52 and the anode 53, and a voltage is applied between the cathode 52 and the anode 53 from the power source 59.

The cathode 52 contains a catalyst for reduction as in the cathode 12 of the first electrochemical cell 11, and a catalyst that can reduce carbon dioxide to carbon monoxide may be used as the catalyst for reduction, and may be appropriately selected from, for example, the group consisting of those listed in the catalyst for reduction (first catalyst), and used. A gas feed line 58 (also referred to as a "third gas feed line") is connected to the first electrochemical compartment 55, and carbon dioxide is fed through the gas feed line 58. In the first electrochemical compartment 55, carbon dioxide is first fed to the first electrochemical compartment 55, and carbon dioxide fed is reduced on the cathode 52, to produce carbon monoxide. Carbon monoxide produced may be fed to the second electrochemical compartment 56 of the second electrochemical cell 51 through a connecting path 57 that connects the first electrochemical compartment 55 (namely, a region at the side of the cathode) of the second electrochemical cell 51 and the second electrochemical compartment 16 (a region at the side of the anode) of the first electrochemical cell 11. That is, the connecting path 57 serves as a first gas feed line that feeds carbon monoxide to the first electrochemical cell 11.

The anode 53 of the second electrochemical cell 51 may contain a catalyst that can oxidize an oxidizable substance, and the catalyst may be appropriately selected from the group consisting of those listed as the second catalyst, and used, or a catalyst other than those listed as the second catalyst may be used. When the carbonate compound is produced from the alcohol-based compound (1) in the second electrochemical compartment 56, as described below, a third catalyst that catalyzes the reaction may be contained in the second electrochemical compartment 56. The detailed description of the second catalyst and the third catalyst is as described above, and the detail is omitted.

The oxidizable substance, to be oxidized at the side of the anode 53, may be water or may be the alcohol-based compound (1) as in the first electrochemical cell 11. When the alcohol-based compound (1) is used as the oxidizable substance, the carbonate compound is produced also in the second electrochemical cell 51 as in the first electrochemical cell 11 of the first embodiment. The carbonate compound produced may be used to produce the first product, the second product, and the like in a reactor different from the second electrochemical cell 51, as in each of the embodiments, and the alcohol-based compound (1) eliminated in the reactor may be fed to the second electrochemical cell 51 or the like and used as a raw material.

Also in the above fifth embodiment, not only the carbonate compound produced in the first electrochemical cell 11 is converted into the first product in the first reactor 21, but also the alcohol-based compound (1) eliminated in the first reactor 21 is recycled in the region at the side of the anode (second electrochemical compartment 16) of the first electrochemical cell 11, and therefore the target product can be efficiently produced.

Sixth Embodiment

Next, a sixth embodiment of the present invention will be described.

While carbon monoxide is fed from the carbon monoxide source to the side of the anode of the first electrochemical cell 11 in the second embodiment, the second electrochemical cell 51 is provided and carbon monoxide produced in the second electrochemical cell 51 is fed to the side of the anode of the first electrochemical cell 11 as in the fifth embodiment, in a synthesis system 60 of the sixth embodiment, as illustrated in FIG. 7.

Hereinafter, the fifth embodiment will be described with respect to differences from the second embodiment.

The second electrochemical cell 51 has the configuration as described in the fifth embodiment, and carbon monoxide produced at the side of the cathode of the second electrochemical cell 51 is fed to the second electrochemical compartment 56 of the first electrochemical cell 11 through the connecting path 57.

Also in the sixth embodiment, not only the carbonate compound produced in the first electrochemical cell 11 is converted into the first product in the first reactor 21, but also the first product is fed to the second reactor 22, and the second product is produced in the second reactor 22. The alcohol-based compounds (1) eliminated in the first and second reactors 21 and 22 are fed to the region at the side of the anode (second electrochemical compartment 16) of the first electrochemical cell 11, and therefore the target product can be efficiently produced, as in the second embodiment.

While an aspect in which all carbon monoxide fed to the region at the side of the anode (second electrochemical compartment 16) of the first electrochemical cell 11 is fed from the region at the side of the cathode (first electrochemical compartment 15) of the second electrochemical cell 51 in the above fifth and sixth embodiments, a part of such carbon monoxide may be fed from the second electrochemical cell 51 and another part thereof may be fed from another carbon monoxide source. For example, a part of carbon monoxide may be fed from the region at the side of the cathode (first electrochemical compartment 15) of the first electrochemical cell 11 or may be fed from another carbon monoxide source as described in the third and fourth embodiments.

While the electrochemical cell 11 is configured to have a membrane-electrode assembly in each of the above embodiments, it is not limited to such configuration, and an ion conducting membrane and both electrodes may be disposed at positions away from each other. In this case, for example, the electrochemical cell may be filled with an electrolyte solution, an ion conducting membrane may be provided so as to partition the electrolyte solution, and the cathode and the anode may be disposed in the respective electrolyte solutions in the regions partitioned by the ion conducting membrane. Much the same is true on the electrochemical cell 51.

According to the foregoing present invention, an organic compound can be efficiently and practically synthesized by recycle of a by-product of an organic compound produced in a subsequent reaction, for an electrochemical reaction, in a synthesis method and a synthesis system where carbon monoxide is adopted as a starting material.

EXAMPLES

The present invention will be described in more detail with reference to Examples, but the present invention is not intended to be limited by these Examples at all.

Example 1

300 mg of $Co(II)(NO_3)_2$ was dissolved in and mixed with 50 ml of ethanol, thereby providing a cobalt complex solution. Next, 30 mg of 4,4'-bipyridine was mixed with 40 ml of ethanol, 1.7 ml of the cobalt complex solution and 160 mg of mesoporous carbon were added thereto, and the resultant was dried and then calcinated under an argon atmosphere at 400° C. for 2 hours, thereby providing a cathode catalyst powder. 30 mg of the cathode catalyst powder and 3 mg of PTFE were dispersed in 0.3 mL of isopropanol, and carbon paper was coated with the resulting dispersion. The resultant was heated and dried at 80° C. for 1 hour, thereby providing a cathode.

Subsequently, 70 mg of $PdCl_2$ (manufactured by Sigma-Aldrich) and 150 mg of mesoporous carbon (manufactured by Sigma-Aldrich) were dispersed in 50 ml of ion-exchange water, and dried, and then calcinated at 400° C., thereby providing an anode catalyst. 30 mg of the anode catalyst and 3 mg of PTFE were dispersed in 0.5 ml of isopropanol, carbon paper was coated with the resulting dispersion, and the resultant was dried at 80° C. for 1 hour, thereby providing an anode.

The resulting cathode and anode were stacked on an ion conducting membrane made of Nafion (trade name), and hot-pressed at 59 MPa and 413 K, thereby producing a membrane-electrode assembly. The membrane-electrode assembly was placed at the center of a two-chamber diaphragm cell having spaces for a first electrochemical compartment and a second electrochemical compartment, thereby providing a first electrochemical cell. In addition, first and second reactors were prepared, thereby preparing the synthesis system according to the second embodiment.

The first electrochemical compartment was filled with water, and the second electrochemical compartment was filled with, as a filling liquid, methanol (alcohol-based compound (1)) containing 0.2 mol/L of LiBr (manufactured by Sigma-Aldrich) as an electrolyte salt. Thereafter, an electrochemical reaction was performed for 1 hour by applying a voltage of 3.0 V between the cathode and the anode under an environment of 273 K (0° C.) with flowing of carbon monoxide at 10 ml/L. Thereafter, analysis by gas chromatography was made, and it could be confirmed that dimethyl carbonate (DMC, selection rate: 90%) and dimethoxymethane (DMM, selection rate: 10%) as products were produced.

Next, the filling liquid containing DMC and DMM, placed in the second electrochemical compartment, was extracted, and purified by a distillation apparatus, and DMC was separated. DMC separated from the distillation apparatus, and furthermore 1,4-butanediamine, and 1,5,7-triazabicyclo[4.4.0]dec-5-ene (TBD) as a catalyst were fed to the first reactor at a molar ratio of 2/1/0.1, and reacted at 80° C. for 6 hours.

Water was mixed with the resulting liquid reactant, and an organic layer was then separated and thereafter concentrated by evaporation, thereby providing a powder. The resulting powdery dimethyl-1,4-butylenedicarbamate (compound represented by the formula (5-1) where $R^2$ represented a 1,4-butylene group) was recovered. Methanol as a by-product was again fed to the second electrochemical compartment.

The dimethyl-1,4-butylenedicarbamate recovered, and furthermore 1,4-butanediamine and $K_2CO_3$ were fed to the second reactor so that the molar ratio was 1/1/0.05, and reacted at 160° C. for 6 hours. The resulting liquid reactant was heated in a reduced-pressure atmosphere, to thereby separate the solvent, thereby providing polyurethane 1 represented by formula (5-3) where $R^2$ represented a 1,4-butylene group, as a target product. Methanol as a by-product was again fed to the second electrochemical compartment.

Example 2

Polyurethane 2 as a target product was obtained in the same manner as in Example 1 except that the diamine-based compound was changed from 1,4-butanediamine to 1,4-hexanediamine in Example 1. Polyurethane 2 was a compound represented by the formula (5-3) where $R^2$ represented a 1,4-hexylene group.

Example 3

Polyurethane 3 as a target product was obtained in the same manner as in Example 1 except that 1,4-butanediamine was changed to 1,4-decanediamine in Example 1. Polyurethane 3 was a compound represented by the formula (5-3) where $R^2$ represented a 1,4-decylene group.

Example 4

A synthesis system of the first embodiment was prepared in the same manner as in Example 1 except that the second reactor was omitted. In the first electrochemical cell, carbon monoxide was flown into the second electrochemical compartment to perform the same electrochemical reaction as in Example 1, and DMC was separated using the distillation apparatus.

DMC from the distillation apparatus, and furthermore 1,4-butanediol as a diol-based compound and 4-dimethylaminopyridine as a catalyst were fed to the first reactor so that the molar ratio was 1/1/0.01, and reacted at 130° C. for 1 hour and further reacted at 170° C. for 1 hour under reduced pressure, thereby providing a liquid reactant. Here, the reaction was allowed to progress under reduced pressure while the solvent containing methanol as a by-product being removed by distillation, thereby providing a solid as a product. The solvent removed by distillation was subjected to distillation to thereby allow methanol to be recovered, and methanol recovered was again fed to the second electrochemical compartment.

The resulting liquid reactant was heated in a reduced-pressure atmosphere to thereby separate the solvent, and recrystallization was conducted for purification, thereby providing polycarbonate 1 represented by the formula (4-3) where $R^1$ represented a 1,4-butylene group, as a target product.

Example 5

A synthesis system according to the second embodiment was prepared in the same manner as in Example 1. In the first electrochemical cell, carbon monoxide was flown into the second electrochemical compartment to perform the same electrochemical reaction as in Example 4, and DMC was separated using the distillation apparatus.

DMC from the distillation apparatus, and also bisphenol A as a diol-based compound and $Bu_2SnO$ as a catalyst were fed to the first reactor so that the molar ratio was 10/1/0.02, and reacted at 160° C. for 48 hours. The resulting liquid reactant was heated in a reduced-pressure atmosphere to thereby separate the solvent, and bisphenol A bis(methyl carbonate) (BPAMC) represented by the formula (4-1) where $R^1$ was represented by the following formula was recovered. Methanol as a by-product was again fed to the second electrochemical compartment.

BPAMC recovered in the second reactor, and $Bu_2SnO$ were fed so that the molar ratio was 1/0.5, and reacted at 220° C. for 2 hours under vacuum, thereby providing a liquid reactant. Here, the reaction was allowed to progress under reduced pressure while methanol as a by-product being removed by distillation, and methanol recovered was again fed to the second electrochemical compartment.

The resulting liquid reactant was dissolved in dichloromethane, and thereafter methanol was added thereto, thereby providing a powder. Furthermore, recrystallization was conducted for purification, thereby providing polycarbonate 2 represented by the formula (4-3) where $R^1$ was represented by the following formula, as a target product.

[Formula 1]

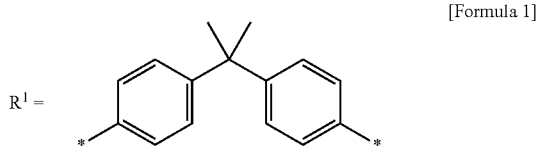 [SMILES: *c1ccc(C(C)(C)c2ccc(*)cc2)cc1]

In the above formula, * represented a binding position to an oxygen atom.

Example 6

Polycarbonate 3 was obtained in the same manner except that bisphenol A was changed to m,m'-bisguaiacol in Example 5. Polycarbonate 3 was polycarbonate represented by the formula (4-3) where $R^1$ was represented by the following formula.

[Formula 2]

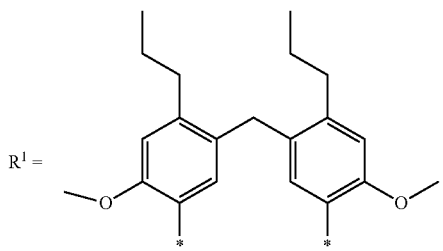

R¹ =

In the above formula, * represented a binding position to an oxygen atom.

Example 7

A first electrochemical cell was prepared and first and second reactors were further prepared in the same manner as in Example 1. The first electrochemical compartment and the second electrochemical compartment were connected by a Teflon tube to form a first connecting path, thereby preparing a synthesis system of the fourth embodiment.

$CO_2$ (1 atm) was allowed to flow through the first electrochemical compartment, and the second electrochemical compartment was filled with methanol containing 0.2 mol/L of LiBr (manufactured by Sigma-Aldrich) as an electrolyte salt. A voltage of 3.0 V was applied between a first electrode and a second electrode under an environment of 273 K, and an electrochemical reaction was performed for 1 hour. During the reaction, a product (carbon monoxide) produced in the first electrochemical compartment was flown into the second electrochemical compartment, and DMC was produced in the second electrochemical compartment. Thereafter, analysis by gas chromatography was made, and it could be confirmed that dimethyl carbonate (DMC, selection rate: 90%) and dimethoxymethane (DMM, selection rate: 10%) as products were produced.

Next, the filling liquid containing DMC and DMM, placed in the second electrochemical compartment, was extracted, and purified by a distillation apparatus, and DMC was separated. DMC separated from the distillation apparatus, and furthermore 1,4-butanediamine, and 1,5,7-triazabicyclo[4.4.0]dec-5-ene (TBD) as a catalyst were fed to the first reactor at a molar ratio of 2/1/0.1, and reacted at 80° C. for 6 hours.

Water was mixed with the resulting liquid reactant, an organic layer was then separated, and thereafter concentrated and separated by evaporation, and powdery dimethyl-1,4-butylenedicarbamate (compound represented by the formula (5-1) where $R^2$ represented a 1,4-butylene group) was recovered. Methanol as a by-product was again fed to the second electrochemical compartment.

The dimethyl-1,4-butylenedicarbamate recovered, and furthermore 1,4-butanediamine and $K_2CO_3$ were fed to the second reactor so that the molar ratio was 1/1/0.05, and reacted at 160° C. for 6 hours.

The resulting liquid reactant was heated in a reduced-pressure atmosphere, to thereby separate the solvent, thereby providing polyurethane 1 represented by formula (5-3) where $R^2$ represented a 1,4-butylene group, as a target product. Methanol as a by-product was again fed to the second electrochemical compartment.

Example 8

Polyurethane 2 as a target product was obtained in the same manner as in Example 1 except that 1,4-butanediamine was changed to 1,4-hexanediamine in Example 1. Polyurethane 2 was a compound represented by the formula (5-3) where $R^2$ represented a 1,4-hexylene group.

Example 9

A synthesis system of the third embodiment was prepared in the same manner as in Example 7 except that the second reactor was omitted. In the first electrochemical cell, carbon monoxide was flown into the second electrochemical compartment to perform the same electrochemical reaction as in Example 7, and DMC was separated using the distillation apparatus.

DMC from the distillation apparatus, 1,4-butanediol as a diol-based compound and 4-dimethylaminopyridine as a catalyst were fed to the first reactor so that the molar ratio was 1/1/0.01, and reacted at 130° C. for 1 hour and further reacted at 170° C. for 1 hour under reduced pressure, thereby providing a liquid reactant. Here, the reaction was allowed to progress under reduced pressure while methanol as a by-product being removed by distillation, and methanol recovered was again fed to the second electrochemical compartment.

The resulting liquid reactant was heated in a reduced-pressure atmosphere to thereby separate the solvent, and recrystallization was conducted for purification, thereby providing polycarbonate 1 represented by the formula (4-3) where $R^1$ represented a 1,4-butylene group, as a target product.

Example 10

A synthesis system was prepared in the same manner as in Example 7. In the first electrochemical cell, carbon monoxide was flown into the second electrochemical compartment to perform the same electrochemical reaction as in Example 7, and DMC was separated using the distillation apparatus.

DMC from the distillation apparatus, and furthermore bisphenol A as a diol-based compound and $Bu_2SnO$ as a catalyst were fed to the first reactor so that the molar ratio was 10/1/0.02, and reacted at 160° C. for 48 hours.

The resulting liquid reactant was heated in a reduced-pressure atmosphere to thereby separate the solvent, and bisphenol A bis(methyl carbonate) (BPAMC) represented by the formula (4-1) where $R^1$ was represented by the following formula was recovered. Methanol as a by-product was again fed to the second electrochemical compartment.

BPAMC recovered in the second reactor, and $Bu_2SnO$ were fed so that the molar ratio was 1/0.5, and reacted at 220° C. for 2 hours under vacuum, thereby providing a liquid reactant. Here, the reaction was allowed to progress under reduced pressure while methanol as a by-product being removed by distillation, and methanol recovered was again fed to the second electrochemical compartment.

The resulting liquid reactant was heated in a reduced-pressure atmosphere to thereby separate the solvent, and recrystallization was conducted for purification, thereby providing polycarbonate 2 represented by the formula (4-3) where $R^1$ was represented by the following formula, as a target product.

[Formula 3]

R¹ = 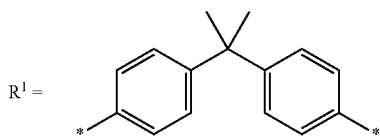

In the above formula, * represented a binding position to an oxygen atom.

Example 11

A synthesis system according to the sixth embodiment, including a second electrochemical cell produced as described below, in addition to the first electrochemical cell, and the first and second reactors in Example 1, was prepared.

300 mg of Co(II) (NO$_3$)$_2$ was dissolved in and mixed with 50 ml of ethanol, thereby providing a cobalt complex solution. Next, 30 mg of 4,4'-bipyridine was mixed with 40 ml of ethanol, 1.7 ml of the cobalt complex solution and 160 mg of mesoporous carbon were added thereto, and the resultant was dried and then calcinated under an argon atmosphere at 400° C. for 2 hours, thereby providing a cathode catalyst powder. 30 mg of the cathode catalyst powder and 3 mg of PTFE were dispersed in 0.3 mL of isopropanol, and carbon paper was coated with the resulting dispersion. The resultant was heated and dried at 80° C. for 1 hour, thereby providing a cathode.

Subsequently, 70 mg of Ir(III)Cl$_3$ (manufactured by Sigma-Aldrich) and 150 mg of mesoporous carbon (manufactured by Sigma-Aldrich) were dispersed in 50 ml of ion-exchange water, and dried, and then calcinated at 400° C., thereby providing an anode catalyst. 30 mg of the anode catalyst and 3 mg of PTFE were dispersed in 0.5 ml of isopropanol, carbon paper was coated with the resulting dispersion, and the resultant was dried at 300° C. for 1 hour, thereby providing an anode.

The resulting cathode and anode were stacked on an ion conducting membrane made of Nafion (trade name), and hot-pressed at 59 MPa and 413 K, thereby producing a membrane-electrode assembly. The membrane-electrode assembly was placed at the center of a two-chamber diaphragm cell having spaces for a first electrochemical compartment and a second electrochemical compartment, thereby providing a second electrochemical cell. The second electrochemical compartment of the second electrochemical cell was filled with water.

A voltage of 3.0 V was applied between the cathode and the anode of the second electrochemical cell under an environment of 273 K. The product gas in the first electrochemical compartment was analyzed by gas chromatography, and it was confirmed that carbon monoxide (selection rate: 85%) as a product was produced.

The product gas was fed to the second electrochemical compartment of the first electrochemical cell through a gas feed line with bubbling. The subsequent process was performed in the same manner as in Example 1, thereby providing polyurethane 1. Also in Example 11, methanol eliminated in the first and second reactors was again fed to the second electrochemical compartment of the first electrochemical cell.

Example 12

Polyurethane 2 as a target product was obtained in the same manner as in Example 1 except that the diamine-based compound was changed from 1,4-butanediamine to 1,4-hexanediamine in Example 11.

Example 13

A synthesis system according to the fifth embodiment was prepared in the same manner as in Example 11 except that no second reactor was prepared.

The product gas produced in the second electrochemical cell in the same manner as in Example 11 was fed to the second electrochemical compartment of the first electrochemical cell through a gas feed line with bubbling in the same manner as in Example 4. The subsequent process was performed in the same manner as in Example 4, thereby providing polycarbonate 1. Also in Example 13, methanol eliminated in the first reactor could be again fed to the second electrochemical compartment of the first electrochemical cell.

Example 14

A synthesis system according to the sixth embodiment was prepared in the same manner as in Example 11. The product gas produced in the second electrochemical cell was fed to the second electrochemical compartment of the first electrochemical cell through a gas feed line with bubbling in the same manner as in Example 11. The subsequent process was performed in the same manner as in Example 5, thereby providing polycarbonate 2. Also in Example 14, methanol eliminated in the first and second reactors could be again fed to the second electrochemical compartment of the first electrochemical cell.

As described above, in each Example, the carbonate compound obtained in the first electrochemical cell could be used to produce various target products in the first reactor or the first and second reactors by a dealcoholization reaction, thereby allowing alcohol eliminated to be recycled in the first electrochemical cell, and therefore each target product could be efficiently synthesized.

REFERENCE SINGS LIST 10, 30, 35, 40, 50, 60: synthesis system
11: first electrochemical cell
12: cathode
13: anode
15: first electrochemical compartment
16: second electrochemical compartment
17: gas feed line
20: circulation line
20A: discharge line
20B: feed pathway
21: first reactor
22: second reactor
51: second electrochemical cell

The invention claimed is:
1. A synthesis method comprising:
a first step of producing a carbonate compound from carbon monoxide and an alcohol-based compound at a side of an anode of a first electrochemical cell comprising a cathode and the anode, wherein a voltage is applied between the cathode and the anode; and
a second step of synthesizing a first product by a dealcoholization reaction of the carbonate compound, wherein an alcohol-based compound eliminated in the second step is recycled in the first step, wherein carbon dioxide is fed to a side of the cathode of the first electrochemical cell, and wherein at least a part of the carbon monoxide used in the first step is produced by reduction of the carbon dioxide at the side of the cathode of the first electrochemical cell.

2. The synthesis method according to claim 1, wherein the carbonate compound is at least one selected from the group consisting of dimethyl carbonate, diethyl carbonate, ethylene carbonate, dipropyl carbonate, propylene carbonate, ethyl methyl carbonate, methyl propyl carbonate, ethyl propyl carbonate and diphenyl carbonate.

3. The synthesis method according to claim 1, wherein the dealcoholization reaction is a dealcoholization condensation reaction of the carbonate compound with at least one selected from the group consisting of a diol-based compound and a diamine-based compound.

4. The synthesis method according to claim 3, wherein the first product is at least one selected from the group consisting of compounds represented by the following formulae (4-1) and (5-1):

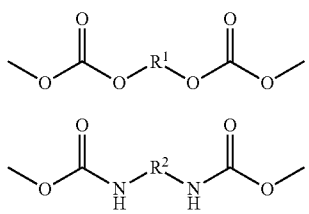

(4-1)

(5-1)

wherein $R^1$ and $R^2$ each independently represent an organic group having 1 to 30 carbon atoms.

5. The synthesis method according to claim 3, wherein the first product is a polymer having at least any of repeating units represented by the following formulae (4-2) and (5-2):

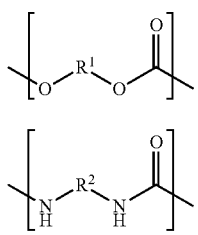

(4-2)

(5-2)

wherein $R^1$ and $R^2$ each independently represent an organic group having 1 to 30 carbon atoms.

6. The synthesis method according to claim 1, wherein the second step is performed in a first reactor, the method further comprises a third step of synthesizing a second product by a further dealcoholization reaction of the first product in a second reactor that is a separate reactor from the first reactor, and an alcohol-based compound eliminated in the third step is recycled in the first step.

7. The synthesis method according to claim 6, wherein the second product is a polymer having at least any of repeating units represented by the following formulae (4-2) and (5-2):

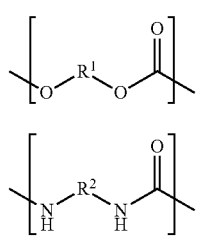

(4-2)

(5-2)

wherein $R^1$ and $R^2$ each independently represent an organic group having 1 to 30 carbon atoms.

8. The synthesis method according to claim 1, wherein at least a part of the carbon monoxide is produced at a side of a cathode of a second electrochemical cell that is a separate electrochemical cell from the first electrochemical cell.

9. The synthesis method according to claim 1, further comprising allowing the carbon monoxide produced in the side of the cathode to flow out into the side of the anode through a connecting path that connects the side of the anode and the side of the cathode.

10. The synthesis method according to claim 1, wherein the dealcoholization reaction is a dealcoholization condensation reaction of the carbonate compound with at least one bisphenol-based compound.

11. The synthesis method according to claim 1, wherein the dealcoholization reaction is a dealcoholization condensation reaction of the carbonate compound with at least one diamine-based compound.

12. The synthesis method according to claim 1,
wherein the first product is synthesized in a first reactor, and
wherein the method further comprises feeding the carbonate compound produced at the side of the anode to the first reactor and the alcohol-based compound eliminated in the first reactor to the side of the anode with using a circulation line.

13. The synthesis method according to claim 12, wherein the circulation line comprises a discharge line that discharges the carbonate compound from the side of the anode, and a feed pathway that feeds the alcohol-based compound eliminated in the first reactor to the side of the anode.

* * * * *